United States Patent
Lui et al.

(10) Patent No.: US 10,988,742 B2
(45) Date of Patent: Apr. 27, 2021

(54) PENICILLIN EXPANDASE MUTANTS, DNA CODING THE MUTANTS, REAGENT KIT CONTAINING THE MUTANTS AND THE APPLICATION

(71) Applicant: BioRight Worldwide Co., Ltd., Road Town (VG)

(72) Inventors: Yuk Sun Lui, Hong Kong (CN); Shiu Ming Cheng, Hong Kong (CN); Yau Lung Siu, Hong Kong (CN); Jun Wang, Hong Kong (CN)

(73) Assignee: BioRight Worldwide Co., Ltd., Road Town (VG)

( * ) Notice: Subject to any disclaimer, the term of this patent is extended or adjusted under 35 U.S.C. 154(b) by 119 days.

(21) Appl. No.: 16/094,625

(22) PCT Filed: Mar. 23, 2017

(86) PCT No.: PCT/CN2017/077858
§ 371 (c)(1),
(2) Date: Oct. 18, 2018

(87) PCT Pub. No.: WO2017/181809
PCT Pub. Date: Oct. 26, 2017

(65) Prior Publication Data
US 2019/0106685 A1 Apr. 11, 2019

(30) Foreign Application Priority Data
Apr. 18, 2016 (CN) .......................... 201610239821.X

(51) Int. Cl.
*C12N 9/02* (2006.01)
*C12P 35/00* (2006.01)
*C12P 37/00* (2006.01)

(52) U.S. Cl.
CPC ............ *C12N 9/0071* (2013.01); *C12P 35/00* (2013.01); *C12P 37/00* (2013.01); *C12Y 114/20001* (2013.01)

(58) Field of Classification Search
CPC ........ C12N 9/0071; C12P 35/00; C12P 37/00; C12Y 114/20001
See application file for complete search history.

(56) References Cited

U.S. PATENT DOCUMENTS 6,905,854 B2 6/2005 Yunn-Bor et al.

FOREIGN PATENT DOCUMENTS

| CN | 1446908 A | 10/2003 |
|---|---|---|
| CN | 1448506 A | 10/2003 |
| CN | 1965083 A | 5/2007 |
| CN | 101040043 A | 9/2007 |
| WO | 9802551 | 1/1998 |
| WO | WO 2005/103261 A1 * | 3/2005 |
| WO | 2007023369 A1 | 3/2007 |

OTHER PUBLICATIONS

Junjie Ji et al. New strategy of site-directed mutagenesis identifies new sites to improve *Streptomyces clavuligerus* deacetoxy-cephalosporin C synthase activity toward penicillin G. Appl Microbiol Biotechnol (2012) 93:2395-2401.*

Kimura et al. Molecular analysis of the gene cluster involved in cephalosporin biosynthesis from Lysobacter lactanngenus YK90. Appl Microbiol Biotechnol (1996) 44:589-596.*

Samson et al. Cloning and expression of the fungal expandase/hydroxylase gene involved in cephalosporin biosynthesis. Biotechnology (N. Y) 5: 1207-1214 (1987).*

Ji, "Research Progress of Directed Modification of Streptomyces Clavuligerus Penicillin Expandase", China Academic Journal, 2013, vol. 41(7), pp. 13-15 (cited in attached International Search Report).

Kovacevic et al, "Accession No. P18548.1", Genbank, Nov. 11, 2015 (cited in attached International Search Report).

Ji et al., "Iterative Combinatorial Mutagenesis as an Effective Strategy for Generation of Deacetoxycephalosporin C Synthase with Improved Activity Toward Penicillin G", Applied and Environmental Microbiology, pp. 7809-7812, vol. 78, No. 21.

* cited by examiner

*Primary Examiner* — Iqbal H Chowdhury
(74) *Attorney, Agent, or Firm* — The Webb Law Firm

(57) ABSTRACT

Provided herein are penicillin expandase mutants, DNA coding the mutants, reagent kit containing the mutants and the application. The penicillin expandase mutants using SEQ ID NO.: 2 in the Sequence Listing as a reference sequence, have at least one amino acid mutation at residue positions corresponding to threonine at position 42 and glutamine at position 126, wherein, amino acid at position 42 is substituted by any other natural amino acid except threonine, amino acid at position 126 is substituted by any other natural amino acid except glutamine. The penicillin expandase mutants of present invention have increased its thermostability and catalytic activity; it is more suitable for commercial and industrial applications.

7 Claims, No Drawings
Specification includes a Sequence Listing.

PENICILLIN EXPANDASE MUTANTS, DNA CODING THE MUTANTS, REAGENT KIT CONTAINING THE MUTANTS AND THE APPLICATION

CROSS-REFERENCE TO RELATED APPLICATIONS

This application is the United States national phase of International Application No. PCT/CN2017/077858 filed Mar. 23, 2017, and claims priority to Chinese Patent Application No. 201610239821.X filed Apr. 18, 2016, the disclosures of which are hereby incorporated in their entirety by reference.

The Sequence Listing associated with this application is filed in electronic format via EFS-Web and is hereby incorporated by reference into the specification in its entirety. The name of the text file containing the Sequence Listing is 1806008_ST25.txt. The size of the text file is 59,740 bytes, and the text file was created on Oct. 16, 2018.

FIELD OF THE INVENTION

The present invention belongs to the field of genetic engineering, more specifically, relates to the penicillin expandase mutants, DNA coding the mutants, reagent kit containing the mutants and the application.

BACKGROUND OF THE INVENTION

β-lactam antibiotics are the class of antibiotics widely used for the clinically treatment of bacterial infection. Penicillin and cephalosporin are the two major classes of β-lactam antibiotic. Because of its high efficacy and low toxicity, Penicillin becomes clinically the most widely used antibiotics. However, some problems are exposed due to the extensive use of penicillin, such as its relatively narrow antibacterial spectrum, acid-labile and easily lead to bacteria resistant.

Penicillin and cephalosporin both possess β-lactam characteristics. The basic difference between them is penicillin has a five-membered thiazolidine ring while cephalosporin has a six-membered dihydrothiazine ring fused with the β-lactam ring. Thus, cephalosporin is more resistant to β-lactamase (such as β-lactamase of Staphylococcus aureus) degradation. And, it has several advantages such as high efficacy, low toxicity, board antibacterial spectrum, low allergenic, can be orally administered etc. As a broad-spectrum semisynthetic antibiotic, cephalosporin can be divided into two groups based on the nucleus: 7-aminodesacetoxycephalosporanic acid (7-ADCA) and 7-aminocephalosporanic acid (7-ACA). 7-ADCA is a downstream product of penicillin and it is used as intermediates for the production of cephalexin, cephradine and other cephalosporins.

Currently, industrial production of 7-ADCA from penicillin G rely on conventional chemical reaction. The reaction conditions are harsh, complex and pollutive. On the other hand, production of phenylacetyl-7-amidodesacetoxycephalosporanic acid (G-7-ADCA) from ring expansion of penicillin G using penicillin expandase is a more efficient and environmental friendly method. Therefore, penicillin expandase becomes a major focus of industrial enzymes research. However, the nature substrate of penicillin expandase is penicillin N which is expensive and not easily available. In contrast, penicillin G, a non-native substrate of penicillin expandase, is commercially available at low cost. So scientists have utilized various methods engineering penicillin expandase to increase its catalytic activity toward penicillin G. Since the study of penicillin expandase of Acremonium chrysogenum by Kohsaka at 1976, research of penicillin expandase has developed rapidly. Although penicillin expandase from Streptomyces clavuligerus has a high potential for industrial application, there are still a need to improve its thermostability and catalytic activity toward penicillin G.

SUMMARY OF THE INVENTION

For the purpose to solve the above problems, the present invention provides penicillin expandase mutants, DNA coding the mutants, reagent kit containing the mutants and the application.

Specifically, the present invention provides:

(1) A penicillin expandase mutant characterized by using SEQ ID NO.:2 in the Sequence Listing as a reference sequence, has at least one amino acid mutation at residue positions corresponding to threonine at position 42 and glutamine at position 126, wherein, amino acid at position 42 is substituted by any other natural amino acid except threonine, amino acid at position 126 is substituted by any other natural amino acid except glutamine.

(2) The penicillin expandase mutant according to (1), characterized by mutation at position 42 threonine and mutation at position 126 glutamine.

(3) The penicillin expandase mutant according to (1) or (2), characterized by substitution of threonine at position 42 by cysteine, aspartic acid, glutamic acid, methionine, proline, glutamine or arginine.

(4) The penicillin expandase mutant according to (1) or (2), characterized by substitution of threonine at position 42 by aspartic acid.

(5) The penicillin expandase mutant according to (1) or (2), characterized by substitution of glutamine at position 126 by alanine, phenylalanine, isoleucine, leucine, methionine, asparagine, tryptophan or tyrosine.

(6) The penicillin expandase mutant according to (1) or (2), characterized by substitution of glutamine at position 126 by phenylalanine.

(7) The penicillin expandase mutant according to (1), characterized by having an amino acid sequence of SEQ ID NO.: 4 and wherein Xaa at position 42 represents cysteine, aspartic acid, glutamic acid, methionine, proline, glutamine, or arginine.

(8) The penicillin expandase mutant according to (1), characterized by having an amino acid sequence of SEQ ID NO.: 4 and wherein Xaa at position 126 represents alanine, phenylalanine, isoleucine, leucine, methionine, asparagine, tryptophan, or tyrosine.

(9) The penicillin expandase mutant according to (1), characterized by having an amino acid sequence of SEQ ID NO.: 4 and wherein Xaa at position 42 represents aspartic acid while Xaa at position 126 represents phenylalanine.

(10) A DNA comprising a nucleotide sequence coding the penicillin expandase mutant according to any one of (1)-(9).

(11) An expression vector comprising the DNA according to (10) operatively linked to a promoter.

(12) A host cell containing the expression vector according to (11).

(13) The use of penicillin expandase mutant according to any one of (1)-(9) in the production of G-7-ADCA.

(14) The use according to (13), wherein the penicillin expandase mutant uses penicillin G as substrate.

(15) A method for the production of G-7-ADCA, comprising incubating the penicillin expandase mutant according to any one of (1)-(9) with the substrate for producing G-7-ADCA.

(16) The method according to (15), wherein the substrate is penicillin G.

(17) A kit for producing G-7-ADCA, comprising penicillin expandase mutant according to any one of (1)-(9).

(18) The kit according to (17), wherein the kit further comprises penicillin G.

The present invention has the following advantages and positive effects when compared to the prior art:

The present invention genetically modified penicillin expandase from *Streptomyces clavuligerus* to increase its thermostability and catalytic activity towards penicillin G. When compared with the wild-type penicillin expandase, penicillin expandase mutants in the present invention have increased at least 20% in catalytic activity or 400% in thermostability. Hence, the penicillin expandase mutants in the present invention are more suitable for commercial and industrial applications.

DETAILED DESCRIPTION OF THE INVENTION

The following further illustrated by the detailed description of the specific embodiments of the present invention, but it is not limit to the present invention. Various modifications or improvements can be made by those scientists in accordance with the basic idea of the present invention; all these are within the scope of the present invention.

In order to solve the above problems of the prior art, the inventors of the present invention have conducted extensive in-depth theoretical and experimental research. Using genetic engineering and protein engineering technology, penicillin expandase from *Streptomyces clavuligerus* has been mutated and finally obtaining a series of penicillin expandase mutants with high catalytic activity and high thermostability, it can be used to manufacture G-7-ADCA more effectively.

Specifically, the present invention provides a penicillin expandase mutant characterized by using SEQ ID NO.:2 in the Sequence Listing as a reference sequence, has at least one amino acid mutation at residue positions corresponding to threonine at position 42 and glutamine at position 126, wherein, amino acid at position 42 is substituted by any other natural amino acid except threonine, amino acid at position 126 is substituted by any other natural amino acid except glutamine.

Preferably, the threonine at position 42 mutated to cysteine, aspartic acid, glutamic acid, methionine, proline, glutamine or arginine; more preferably mutated to aspartic acid, glutamic acid, methionine or glutamine, most preferably mutated to aspartic acid.

Preferably, the glutamine at position 126 mutated to alanine, phenylalanine, isoleucine, leucine, methionine, asparagine, tryptophan or tyrosine acid; more preferably mutated to phenylalanine, alanine, isoleucine, methionine or tyrosine, most preferably mutated to phenylalanine.

Preferably, the penicillin expandase mutant has mutations at position 42 threonine and position 126 glutamine.

Preferably, the penicillin expandase mutants having an amino acid sequence as shown in SEQ ID NO.:4. The nucleotide sequence as shown in SEQ ID NO.:3 codes the amino acid sequence shown in SEQ ID NO.:4. Also preferably, Xaa at position 42 in the SEQ ID NO.:4 represents cysteine, aspartic acid, glutamic acid, methionine, proline, glutamine, or arginine, more preferably represents aspartic acid, glutamic acid, methionine or glutamine, most preferably represents aspartic acid. Also preferably, Xaa at position 126 in the SEQ ID NO.:4 represents alanine, phenylalanine, isoleucine, leucine, methionine, asparagine, tryptophan or tyrosine acid; more preferably represents phenylalanine, alanine, isoleucine, methionine or tyrosine, most preferably represents phenylalanine.

In a preferred embodiment of the invention, the penicillin expandase mutant of the present invention has an amino acid sequence as shown in SEQ ID NO.:4 and Xaa at position 42 represents aspartic acid while Xaa at position 126 represents phenylalanine.

The penicillin expandase mutants of present invention can be obtained through site-directed mutagenesis of wild-type *Streptomyces clavuligerus* penicillin expandase using the techniques known in the art. The nucleotide sequence of aforementioned wild-type *Streptomyces clavuligerus* penicillin expandase is shown in SEQ ID NO.:1, amino acid sequence is shown in SEQ ID NO.:2. The GenBank accession number of wild-type *Streptomyces clavuligerus* penicillin expandase is m32324.

The cloning techniques and protocols used are as follow: Using the techniques known in the art to construct plasmid containing the wild type penicillin expandase gene. The desired position to be mutated and the mutated amino acid was then chosen. The plasmid containing wild-type expandase gene was then modified by PCR amplification using primers that contained the altered DNA sequence corresponding to the desired mutation. The DNA fragments containing the desired point mutation were amplified by PCR to produce a full-length expandase gene with the point mutation. The mutated expandase gene was ligated to an appropriate vector and transformed into a suitable host. The transformed hosts were incubated and screened for positive clones having higher expandase activity and thermostability. Finally, plasmid DNA was extracted and its sequence was analyzed to ensure the correct mutations were introduced to the expandase gene.

For the preparation of the penicillin expandase mutants in this invention, any suitable vectors can be used. Suitable vectors include but are not limited to prokaryotic expression vectors pGEMT-Easy, pRSET and pET21: include but are not limited to eukaryotic expression vectors pYD1 and pYES2/GS; include but are not limited to cloning vectors pUC18/19 and pBluescript-SK.

For the preparation of the penicillin expandase mutants in this invention, the mutated penicillin expandase gene can be expressed intra-cellularly in prokaryotic or eukaryotic cells, or can be expressed extra-cellularly in prokaryotic or eukaryotic cells by using any other techniques known in the art.

For the preparation of the penicillin expandase mutants in this invention, the host cells can be prokaryotic or eukaryotic cells. The prokaryotic cells include but are not limited to *E. coli, Bacillus subtilis, Bacillus brevis, Bacillus megaterium, T. saccharolyticum* and *Streptomyces*. The eukaryotic cells include but are not limited to *Saccharomyces cerevisiae* and *Pichia pastoris*.

As used herein, the term "reference sequence", when it is a nucleotide sequence, refers to the sequence of SEQ ID NO.:1 of the Sequence Listing, when it is an amino acid sequence, refers to the sequence of SEQ ID NO.:2 of the Sequence Listing.

The penicillin expandase mutants in this invention can be used in an unpurified crude enzyme form, or in partially purified enzyme form, or as completely purified enzyme preparation.

The penicillin expandase mutants in this invention can use SEQ ID NO.:2 in the Sequence Listing as a reference sequence, have at least one amino acid mutation when compared to the amino acid sequence in SEQ ID NO.:2. Additionally, the mutants' catalytic activity have increased at least 20% compared to wild-type penicillin expandase, preferably increased at least 20%-100%, more preferably increased at least 200%, and/or thermostability have increased at least 400% compared to wild-type penicillin expandase, preferably increased at least 900%, more preferably increased 1700%.

The present invention also provides a DNA, which containing nucleotide sequence of the penicillin expandase mutant of this invention.

The present invention also provides an expression vector comprising DNA according to this invention which is operatively linked to a promoter.

In the present invention, "expression vector" refers to a vector capable of directing the expression of the gene to which it is operatively linked. Through operatively linked the promoter sequence to the DNA in this invention, this promoter may direct the expression of the corresponding peptide according to the present invention. Typically, expression vectors used in genetic engineering can be in the form of a plasmid, the present invention can also comprise other known forms of expression vectors.

A promoter and a DNA encoding the peptide of the invention are "operatively linked" when the promoter is capable of driving expression of the DNA into RNA. Said promoter may be any promoter conventionally used in the field of genetic engineering.

The expression vector in this invention may also comprise other sequences, such as termination sequences, which can be used to improve the level of genetic information and to minimize read through from the desired construct into other sequences within the vector. Further, the expression vector may also have a selectable marker, for example in the form of antibiotic resistance genes; thereby enable screening of the cells carrying these vectors.

The present invention also provides a host cell containing the expression vector of the present invention.

The term "host cell" as used herein refers to the cell that has been introduced an expression vector according to the present invention. The cell may be a prokaryotic cell, for example, and can be used to quickly generate a large amount of the expression vector of the present invention.

Host cells can be transiently or stably transformed by the expression vector of the present invention. Expression vector can be transformed into cells by any technique known in the art, the techniques, including but not limited to: standard bacterial transformation, calcium phosphate coprecipitation or electroporation.

The present invention also provides the use of the penicillin expandase mutants of this invention in the production of G-7-ADCA. Preferably, in the application, the substrate of the penicillin expandase mutant is penicillin G.

The present invention also provides a method for the production of G-7-ADCA, comprising incubating penicillin expandase mutants of the present invention with the substrate for producing G-7-ADCA. Preferably, the substrate is penicillin G.

Preparation of G-7-ADCA can be done by using the techniques known in the art, as long as the penicillin expandase mutants of the present invention are used as a catalyst.

The present invention also provides a kit for the preparation of G-7-ADCA comprising the penicillin expandase mutants of the present invention. Preferably it also contains penicillin G. Those technicians of this field can understand the kit of the present invention can also comprise any other reagents and materials that are required for the preparation of G-7-ADCA.

The following examples are given for the purpose of illustrating this invention but are not limited thereto.

EXAMPLES

Unless specifically stated, conditions should follow common protocols or conditions from materials provide, volume/volume % (v/v %) should be used as the percentage of contents.

Example 1: Cloning of the Wild Type Penicillin Expandase and Construction of pGEMT-SC Plasmid Based on the amino acid sequence of penicillin expandase in the protein sequence database (UniProtKB P18548), the amino acid sequence was reversely translated to the DNA sequence according to the codon usage bias of the host cell using software Gene Designer 2.01. Primers SF and SR were designed based on that DNA sequence (Table 1).

Synthesize the above reverse transcribed DNA sequence and ligated into the vector pMA-T (Life Technologies, Inc.) to obtain plasmid SC-pMA-T. A 936 bp PCR amplified product was obtained by using plasmid SC-pMA-T as a template with SF and SR as primers.

PCR reaction conditions were: 1 µg plasmid SC-pMA-T, 0.1 µg primers (SF+SR), 5 µl 10× buffer solution (200 mM Tris-HCl (pH 8.0), 100 mM KCl, 100 mM $(NH_4)_2SO_4$, 20 mM $MgSO_4$, 1% Triton X-100), 4% DMSO, 4 µl 2.5 mM dNTP, 1 U LA Taq polymerase (TaKaRa company), with sterile water to make up to 50 µl reaction.

PCR amplification profile was as follows: 96 OC 5 min, 30 cycles of: 94° C. 45 seconds, 53° C. 45 seconds, and 72 OC 3 min and finally 72 OC 10 minutes at the end.

The amplified wild-type penicillin expandase gene was purified by 1% (w/v) agarose gel electrophoresis, a 936 bp PCR fragment SC was extracted and purified using EZNA Gel Extraction Kit (Omega Bio-tek Inc.). Fragment SC was ligated to pGEMT-Easy (Promega Corporation) vector by T4 DNA ligase (NEB Inc.) using TA cloning method to obtain plasmid pGEMT-SC. The plasmid was transformed into competent *E. coli* BL21 (Novagen, Inc.). The transformed cell were cultured on LB plate containing 50 mg/L of ampicillin at 37° C. Single colony was picked and plasmid pGEMT-SC was extracted and purified using DNA-spin plasmid DNA purification kit (Intron Biotechnology). The correct sequence was confirmed by DNA sequencing.

Example 2: Site-Directed Mutagenesis of Penicillin Expandase Position 42

"PCR Protocols (John M. S. Bartlett and David Stirling. Totowa, N.J.: Humana Press, 2003)" was used as reference for site-directed mutagenesis techniques.

Plasmid pGEMT-SC (Example 1) was used as a template to design primers 42DF and 42DR (Table 1). Mutant SC-T42D was obtained by substituting threonine (T) by aspartic acid (D) in position 42 of the original amino acid sequence.

Specifically, plasmid pGEMT-SC was used as a template, fragment 42D1 was amplified with primers SF and 42DR. Fragment 42D2 was amplified with primers 42DF and SR. PCR reaction conditions were: 1 µg plasmid pGEMT-SC, 0.1 µg primers (SF+42DR) (fragment 42D1) or 0.1 µg primers (42DF+SR) (fragment 42D2), 5 µl 10× buffer solution (200 mM Tris-HCl (pH 8.0), 100 mM KCl, 100 mM $(NH_4)_2SO_4$, 20 mM $MgSO_4$, 1% Triton X-100), 4% DMSO, 4 µl 2.5 mM dNTP, 1 U LA Taq polymerase (TaKaRa company), with sterile water to make up to 50 µl reaction.

PCR amplification profile was as follows: 96 OC 5 min, 30 cycles of: 94° C. 45 seconds, 53° C. 45 seconds, and 72 OC 60 seconds and finally 72° C. 10 minutes at the end.

The amplified fragments 42D1 and 42D2 were purified by 1% (w/v) agarose gel electrophoresis and EZNA Gel Extraction Kit (Omega Bio-tek Inc.). The full-length gene was amplified with primers SF and SR. PCR reaction conditions were: 50 ng DNA fragment 42D1 and 50 ng DNA fragment 42D2, 0.1 µg primers (SF+SR), 5 µl 10× buffer solution (200 mM Tris-HCl (pH 8.0), 100 mM KCl, 100 mM $(NH_4)_2SO_4$, 20 mM $MgSO_4$, 1% Triton X-100), 4% DMSO, 4 µl 2.5 mM dNTP, 1 U LA Taq polymerase (TaKaRa company), with sterile water to make up to 50 µl reaction.

PCR amplification profile was as follows: 96 OC 5 min, 30 cycles of: 94° C. 45 seconds, 53° C. 45 seconds, and 72 OC 2 min and finally 72 OC 10 minutes at the end.

The full-length mutated gene was purified by 1% (w/v) agarose gel electrophoresis, extracted and purified using EZNA Gel Extraction Kit (Omega Bio-tek Inc.) to obtain a 936 bp full-length mutated gene SC-T42D.

Mutants SC-T42C, SC-T42E, SC-T42M, SC-T42P, SC-T42Q and SC-T42R were constructed using similar methods as described above. Primers used are shown in Table 1 while mutants name and their sequence number are shown in Table 2.

Example 3: Construction of Plasmid PR-SC-T42D

Mutated gene SC-T42D and vector pRSET-KAN (Invitrogen) were digested by NdeI+BglII (NEB). The digested products were purified by 1% (w/v) agarose gel electrophoresis, extracted and purified using EZNA Gel Extraction Kit (Omega Bio-tek Inc.). They were ligated by T4 ligase (NEB) and transformed into competent *E. coli* HB101 (Bio-Rad). The transformed cell were cultured on LB plate containing 50 mg/L of kanamycin at 37° C. Single colony was picked and plasmid PR-SC-T42D was extracted and purified using DNA-spin plasmid DNA purification kit (Intron Biotechnology). The correct sequence was confirmed by DNA sequencing.

Plasmids PR-SC-T42C, PR-SC-T42E, PR-SC-T42M, PR-SC-T42P, PR-SC-T42Q and PR-SC-T42R were constructed using similar methods as described above.

Example 4: Site-Directed Mutagenesis of Penicillin Expandase Position 126

"PCR Protocols (John M. S. Bartlett and David Stirling. Totowa, N.J.: Humana Press, 2003)" was used as reference for site-directed mutagenesis techniques.

Plasmid pGEMT-SC (Example 1) was used as a template to design primers 126FF and 126FR (Table 1). Mutant SC-Q126F was obtained by substituting glutamine (Q) by phenylalanine (F) in position 126 of the original amino acid sequence.

Specifically, plasmid pGEMT-SC was used as a template, fragment 126F1 was amplified with primers SF and 126FR. Fragment 126F2 was amplified with primers 126FF and SR. PCR reaction conditions were: 1 µg plasmid pGEMT-SC, 0.1 µg primers (SF+126FR) (fragment 126F1) or 0.1 µg primers (126FF+SR) (fragment 126F2), 5 µl 10× buffer solution (200 mM Tris-HCl (pH 8.0), 100 mM KCl, 100 mM $(NH_4)_2SO_4$, 20 mM $MgSO_4$, 1% Triton X-100), 4% DMSO, 4 µl 2.5 mM dNTP, 1 U LA Taq polymerase (TaKaRa company), with sterile water to make up to 50 µl reaction.

PCR amplification profile was as follows: 96 OC 5 min, 30 cycles of: 94° C. 45 seconds, 53° C. 45 seconds, and 72 OC 60 seconds and finally 72 OC 10 minutes at the end.

The amplified fragments 126F1 and 126F2 were purified by 1% (w/v) agarose gel electrophoresis and EZNA Gel Extraction Kit (Omega Bio-tek Inc.). The full-length gene was amplified with primers SF and SR. PCR reaction conditions were: 50 ng DNA fragment 126F1 and 50 ng DNA fragment 126F2, 0.1 µg primers (SF+SR), 5 µl 10× buffer solution (200 mM Tris-HCl (pH 8.0), 100 mM KCl, 100 mM $(NH_4)_2SO_4$, 20 mM $MgSO_4$, 1% Triton X-100), 4% DMSO, 4 µl 2.5 mM dNTP, 1 U LA Taq polymerase (TaKaRa company), with sterile water to make up to 50 µl reaction.

PCR amplification profile was as follows: 96 OC 5 min, 30 cycles of: 94° C. 45 seconds, 53° C. 45 seconds, and 72 OC 2 min and finally 72 OC 10 minutes at the end.

The full-length mutated gene was purified by 1% (w/v) agarose gel electrophoresis, extracted and purified using EZNA Gel Extraction Kit (Omega Bio-tek Inc.) to obtain a 936 bp full-length mutated gene SC-Q126F.

Mutants SC-Q126A, SC-Q126I, SC-Q126L, SC-Q126M, SC-Q126N, SC-Q126W and SC-Q126Y were constructed using similar methods as described above. Primers used are shown in Table 1 while mutants name and their sequence number are shown in Table 2.

Example 5: Construction of Plasmid PR-SC-Q126F

Mutated gene SC-Q126F and vector pRSET-KAN (Invitrogen) were digested by NdeI+BglII (NEB). The digested products were purified by 1% (w/v) agarose gel electrophoresis, extracted and purified using EZNA Gel Extraction Kit (Omega Bio-tek Inc.). They were ligated by T4 ligase (NEB) and transformed into competent *E. coli* HB101 (Bio-Rad). The transformed cell were cultured on LB plate containing 50 mg/L of kanamycin at 37° C. Single colony was picked and plasmid PR-SC-Q126F was extracted and purified using DNA-spin plasmid DNA purification kit (Intron Biotechnology). The correct sequence was confirmed by DNA sequencing.

Plasmids PR-SC-Q126A, PR-SC-Q126I, PR-SC-Q126L, PR-SC-Q126M, PR-SC-Q126N, PR-SC-Q126W and PR-SC-Q126Y were constructed using similar methods as described above.

Example 6: Construction of Double Mutant of Penicillin Expandase Plasmid PR-SC-T42DQ126F "PCR Protocols (John M. S. Bartlett and David Stirling. Totowa, N.J.: Humana Press, 2003)" was used as reference for site-directed mutagenesis techniques.

Plasmid PR-SC-T42D (Example 3) was used as a template. Mutant SC-T42DQ126F was obtained by substituting glutamine (Q) by phenylalanine (F) in position 126 of the amino acid sequence.

Specifically, plasmid PR-SC-T42D was used as a template, fragment 42D126F1 was amplified with primers SF and 126FR. Fragment 42D126F2 was amplified with primers 126FF and SR. PCR reaction conditions were: 1 pg plasmid PR-SC-T42D, 0.1 gtg primers (SF+126FR) (fragment 42D126F1) or 0.1 μg primers (126FF+SR) (fragment 42D126F2), 5 μl 10× buffer solution (200 mM Tris-HCl (pH 8.0), 100 mM KCl, 100 mM $(NH_4)_2SO_4$, 20 mM $MgSO_4$, 1% Triton X-100), 4% DMSO, 4 μl 2.5 mM dNTP, 1 U LA Taq polymerase (TaKaRa company), with sterile water to make up to 50 μl reaction.

PCR amplification profile was as follows: 96 OC 5 min, 30 cycles of: 94° C. 45 seconds, 53° C. 45 seconds, and 72 OC 60 seconds and finally 72 OC 10 minutes at the end.

The amplified fragments 42D126F1 and 42D126F2 were purified by 1% (w/v) agarose gel electrophoresis and EZNA Gel Extraction Kit (Omega Bio-tek Inc.). The full-length gene was amplified with primers SF and SR. PCR reaction conditions were: 50 ng DNA fragment 42D126F1 and 50 ng DNA fragment 42D126F2, 0.1 μg primers (SF+SR), 5 μl 10× buffer solution (200 mM Tris-HCl (pH 8.0), 100 mM KCl, 100 mM $(NH_4)_2SO_4$, 20 mM $MgSO_4$, 1% Triton X-100), 4% DMSO, 4 μl 2.5 mM dNTP, 1 U LA Taq polymerase (TaKaRa company), with sterile water to make up to 50 l reaction.

PCR amplification profile was as follows: 96 OC 5 min, 30 cycles of: 94° C. 45 seconds, 53° C. 45 seconds, and 72 OC 2 min and finally 72° C. 10 minutes at the end.

The full-length mutated gene was purified by 1% (w/v) agarose gel electrophoresis, extracted and purified using EZNA Gel Extraction Kit (Omega Bio-tek Inc.) to obtain a 936 bp full-length mutated gene SC-T42DQ126F.

Mutated gene SC-T42DQ126F and vector pRSET-KAN (Invitrogen) were digested by NdeI+BglII (NEB). The digested products were purified by 1% (w/v) agarose gel electrophoresis, extracted and purified using EZNA Gel Extraction Kit (Omega Bio-tek Inc.). They were ligated by T4 ligase (NEB) and transformed into competent *E. coli* HB101 (Bio-Rad). The transformed cell were cultured on LB plate containing 50 mg/L of kanamycin at 37° C. Single colony was picked and plasmid PR-SC-T42DQ126F was extracted and purified using DNA-spin plasmid DNA purification kit (Intron Biotechnology). The correct sequence was confirmed by DNA sequencing.

Example 7: Determination of Penicillin Expandase Catalytic Activity

The wild type penicillin expandase plasmid and various penicillin expandase mutant plasmids described above were transformed into *E. coli* BL21 cells (Novagen, Inc.) and cultured on LB plate containing 50 mg/L kanamycin 37° C. Single colony was picked, cultured in a 3 ml LB broth containing 50 mg/L kanamycin at 37° C., 250 rpm for 8 hours, followed by inoculating 1 ml into 50 ml LB broth containing 50 mg/L kanamycin at 37° C., 250 rpm for 18 hours. Cells were collected by centrifugation and resuspended in 10 mM pH 7.4 sodium phosphate buffer, lysed by cell sonicator (50W) with sonication time for 5 seconds 30 times. Cell debris was removed by centrifugation and supernatant was collected as enzyme solution. The enzyme solution was tested for penicillin expandase catalytic activity, and enzyme expression was determined by SDS-polyacrylamide gel electrophoresis (SDS-PAGE). The following are the details:

490 μl of substrate (10 mM Penicillin G, 20 mM sodium α-ketoglutarate, 4 mM L-sodium ascorbate, 1.8 mM ferrous sulfate heptahydrate, 6 mM sodium phosphate buffer (pH 7.5)) was added to a 1.5 ml microcentrifuge tube, followed by addition of 10 μl enzyme solution. The reaction solution was mixed well and placed in a shaker at 200 rpm 30° C. for 30 minutes. 500 μl of methanol was added to stop the reaction. 200 μl of supernatant was taken and added to 800 μl of water, mixed, followed by HPLC determination of G-7-ADCA concentration and catalytic activity. The following Table 2 shows the comparison of the catalytic activity of wild type penicillin expandase and the penicillin expandase mutants.

HPLC analysis conditions are as follow: HPLC Column: Elite HPLC column (Dalian Elite Analytical Instruments Co., 10DS-BP 5 μm, 4.6 mm×250 mm); mobile phase: (A) 50 mM $KH_2PO_4/K_2HPO_4$ (pH7), 6% acetonitrile, (B) 60% acetonitrile; column temperature: 30° C.; flow rate: 1.0 ml/min; detection wavelength: 210 nm.

Example 8: Determination of Thermostability of Penicillin Expandase

Wild-type penicillin expandase and the various penicillin expandase mutants enzyme solution were prepared according to example 7. 200 μl enzyme solution was added into 1.5 ml microcentrifuge tube and was placed in 45° C. water bath for 30 minutes heat treatment. The samples were centrifuged and supernatant were collected for catalytic activity assay according to example 7. The percentage of remaining catalytic activity of wild-type penicillin expandase and of penicillin expandase mutants were calculated by dividing the activity of heat treated penicillin expandase by activity of untreated penicillin expandase stored at 4° C. The percentage of increased enzyme thermostability was calculated by the following formula. The remaining catalytic activity of the wild-type penicillin expandase and various penicillin expandase mutants after heat treatment were shown in the table 3 below.

$$A=(B-C)/C\times100\%=(B-5\%)/5\%\times100\%$$

Where:
A—Percentage of increased thermostability
B—The remaining activity of penicillin expandase mutant after heat treatment
C—The remaining activity of wild-type penicillin expandase after heat treatment

Example 9: G-7-ADCA Production Using Penicillin G as Substrate

Substrates were prepared with the following final concentration: 10 mM penicillin G, 20 mM sodium α-ketoglutarate, 4 mM sodium L-ascorbate and 1.8 mM ferrous sulfate heptahydrate were dissolved in 90 ml 6 mM pH 7.4 sodium phosphate buffer. 1M NaOH was used to adjust the pH to 6, followed by adding 10 ml enzyme solution. The mixture was placed on magnetic stir plate and stirred at high speed. The reaction was maintained at 30° C. and pH 6.4 for 150 minutes. 0.5 ml sample was taken at 30, 60, 90, 120 and 150 minutes from the reaction and mixed with 0.5 ml of methanol to stop the reaction. The samples were centrifuged at 13000 rpm for 1 min. 200 μl supernatant was taken and added into 800 µl H₂O, mixed, followed by HPLC determination of G-7-ADCA concentration.

HPLC analysis conditions are as follow: HPLC Column: Elite HPLC column (Dalian Elite Analytical Instruments Co., 10DS-BP 5 µm, 4.6 mm×250 mm); mobile phase: (A) 50 mM $KH_2PO_4/K_2HPO_4$ (pH7), 6% acetonitrile, (B) 60% acetonitrile; column temperature: 30° C.; flow rate: 1.0 ml/min; detection wavelength: 210 nm.

The present invention is not limited specifically described in the text above. It may be present in various changes within the scope of the claims. These changes are within the scope of the present invention.

TABLE 1

| Product name | | Primers sequence | |
|---|---|---|---|
| Wild-type | SF: | 5' GACCATATGGATACCACGGTACCGACATTTTC 3' | (SEQ ID NO.: 21) |
| | SR: | 5' GCAAGATCTTTAAGCTTTACTCGTACGACGAATG TTC 3' | (SEQ ID NO.: 22) |
| SC-T42C mutant | 42CF: | 5' GACCGATTGTGGCCTGACAGATTGCGAACTGA AATCT 3' | (SEQ ID NO.: 23) |
| | 42CR: | 5' AGATTTCAGTTCGCAATCTGTCAGGCCACAAT CGGTC 3' | (SEQ ID NO.: 24) |
| SC-T42D mutant | 42DF: | 5' GACCGATTGTGGCCTGACAGATGATGAACTGA AATCT 3' | (SEQ ID NO.: 25) |
| | 42DR: | 5' AGATTTCAGTTCATCATCTGTCAGGCCACAAT CGGTC 3' | (SEQ ID NO.: 26) |
| SC-T42E mutant | 42EF: | 5' GACCGATTGTGGCCTGACAGATGAAGAACTGA AATCT 3' | (SEQ ID NO.: 27) |
| | 42ER: | 5' AGATTTCAGTTCTTCATCTGTCAGGCCACAAT CGGTC 3' | (SEQ ID NO.: 28) |
| SC-T42M mutant | 42MF: | 5' GACCGATTGTGGCCTGACAGATATGGAACTGA AATCT 3' | (SEQ ID NO.: 29) |
| | 42MR: | 5' AGATTTCAGTTCCATATCTGTCAGGCCACAAT CGGTC 3' | (SEQ ID NO.: 30) |
| SC-T42P mutant | 42PF: | 5' GACCGATTGTGGCCTGACAGATCCGGAACTGA AATCT 3' | (SEQ ID NO.: 31) |
| | 42PR: | 5' AGATTTCAGTTCCGGATCTGTCAGGCCACAAT CGGTC 3' | (SEQ ID NO.: 32) |
| SC-T42Q mutant | 42QF: | 5' GACCGATTGTGGCCTGACAGATCAGGAACTGA AATCT 3' | (SEQ ID NO.: 33) |
| | 42QR: | 5' AGATTTCAGTTCCTGATCTGTCAGGCCACAAT CGGTC 3' | (SEQ ID NO.: 34) |
| SC-T42R mutant | 42RF: | 5' GACCGATTGTGGCCTGACAGATCGCGAACTGA AATCT 3' | (SEQ ID NO.: 35) |
| | 42RR: | 5' AGATTTCAGTTCGCGATCTGTCAGGCCACAAT CGGTC 3' | (SEQ ID NO.: 36) |
| SC-Q126A mutant | 126AF: | 5' CTGGACGCAGTATTTTGATCGCGCGTATACC GCCAGT 3' | (SEQ ID NO.: 37) |
| | 126AR: | 5' ACTGGCGGTATACGCGCGATCAAAATACTGC GTCCAG 3' | (SEQ ID NO.: 38) |
| SC-Q126F mutant | 126FF: | 5' CTGGACGCAGTATTTTGATCGCTTTTATACC GCCAGT 3' | (SEQ ID NO.: 39) |
| | 126FR: | 5' ACTGGCGGTATAAAAGCGATCAAAATACTGC GTCCAG 3' | (SEQ ID NO.: 40) |
| SC-Q126I mutant | 126IF: | 5' CTGGACGCAGTATTTTGATCGCATTTATACC GCCAGT 3' | (SEQ ID NO.: 41) |
| | 126IR: | 5' ACTGGCGGTATAAATGCGATCAAAATACTGC GTCCAG 3' | (SEQ ID NO.: 42) |
| SC-Q126L mutant | 126LF: | 5' CTGGACGCAGTATTTTGATCGCCTGTATACC GCCAGT 3' | (SEQ ID NO.: 43) |
| | 126LR: | 5' ACTGGCGGTATACAGGCGATCAAAATACTGC GTCCAG 3' | (SEQ ID NO.: 44) |
| SC-Q126M mutant | 126MF: | 5' CTGGACGCAGTATTTTGATCGCATGTATACC GCCAGT 3' | (SEQ ID NO.: 45) |
| | 126MR: | 5' ACTGGCGGTATACATGCGATCAAAATACTGC GTCCAG 3' | (SEQ ID NO.: 46) |
| SC-Q126N mutant | 126NF: | 5' CTGGACGCAGTATTTTGATCGCAACTATACC GCCAGT 3' | (SEQ ID NO.: 47) |
| | 126NR: | 5' ACTGGCGGTATAGTTGCGATCAAAATACTGC GTCCAG 3' | (SEQ ID NO.: 48) |
| SC-Q126W mutant | 126WF: | 5' CTGGACGCAGTATTTTGATCGCTGGTATACC GCCAGT 3' | (SEQ ID NO.: 49) |
| | 126WR: | 5' ACTGGCGGTATACCAGCGATCAAAATACTGC GTCCAG 3' | (SEQ ID NO.: 50) |
| SC-Q126Y mutant | 126YF: | 5' CTGGACGCAGTATTTTGATCGCTATTATACC GCCAGT 3' | (SEQ ID NO.: 51) |
| | 126YR: | 5' ACTGGCGGTATAATAGCGATCAAAATACTGC GTCCAG 3' | (SEQ ID NO.: 52) |

TABLE 2

Comparison of the catalytic activity of wild type penicillin expandase and the penicillin expandase mutants

| Sequence List Number | Name of enzyme | Catalytic activity (%) |
|---|---|---|
| SEQ ID NO.: 2 | Wild-type | 100 |
| SEQ ID NO.: 5 | SC-T42C | 120 |
| SEQ ID NO.: 6 | SC-T42D | 160 |
| SEQ ID NO.: 7 | SC-T42E | 150 |
| SEQ ID NO.: 8 | SC-T42M | 130 |
| SEQ ID NO.: 9 | SC-T42P | 120 |
| SEQ ID NO.: 10 | SC-T42Q | 140 |
| SEQ ID NO.: 11 | SC-T42R | 120 |
| SEQ ID NO.: 12 | SC-Q126A | 210 |
| SEQ ID NO.: 13 | SC-Q126F | 260 |
| SEQ ID NO.: 14 | SC-Q126I | 200 |
| SEQ ID NO.: 15 | SC-Q126L | 180 |
| SEQ ID NO.: 16 | SC-Q126M | 220 |
| SEQ ID NO.: 17 | SC-Q126N | 150 |
| SEQ ID NO.: 18 | SC-Q126W | 120 |

TABLE 2-continued

Comparison of the catalytic activity of wild type penicillin expandase and the penicillin expandase mutants

| Sequence List Number | Name of enzyme | Catalytic activity (%) |
|---|---|---|
| SEQ ID NO.: 19 | SC-Q126Y | 240 |
| SEQ ID NO.: 20 | SC-T42DQ126F | 300 |

TABLE 3

Remaining catalytic activity of wild-type penicillin expandase and various penicillin expandase mutants after heat treatment

| Name of enzyme | Remaining activity (%) after heat treatment at 45° C. for 30 mins | Increased enzyme thermostability (%) |
|---|---|---|
| Wild-type | 5 | — |
| SC-T42D | 25 | 400 |
| SC-T42E | 25 | 400 |
| SC-Q126A | 53 | 960 |
| SC-Q126F | 86 | 1620 |
| SC-Q126I | 60 | 1100 |
| SC-Q126L | 82 | 1540 |
| SC-Q126M | 85 | 1600 |
| SC-Q126Y | 50 | 900 |
| SC-T42DQ126F | 90 | 1700 |

The invention claimed is:

1. A penicillin expandase mutant of wild-type penicillin expandase of SEQ ID NO: 2, wherein the mutation of the mutant is as follows: the amino acid at position 126 is substituted by phenylalanine and, optionally, the amino acid at position 42 is substituted by cysteine, aspartic acid, glutamic acid, methionine, proline, glutamine, or arginine.

2. The penicillin expandase mutant of claim 1, wherein the amino acid sequence of the mutant is as shown by SEQ ID NO: 4, and wherein Xaa at position 42 represents cysteine, aspartic acid, glutamic acid, methionine, proline, glutamine, or arginine, and Xaa at position 126 represents phenylalanine.

3. The penicillin expandase mutant of claim 1, wherein the amino acid sequence of the mutant is as shown by SEQ ID NO: 4, and wherein Xaa at position 42 represents aspartic acid while Xaa at position 126 represents phenylalanine.

4. A kit for phenylacetyl-7-amidodesacetoxycephalosporanic acid (G-7-ADCA), comprising a penicillin expandase mutant of claim 1.

5. The kit of claim 4, wherein the kit further comprises penicillin G.

6. A method for the production of phenylacetyl-7-amidodesacetoxycephalosporanic acid (G-7-ADCA), comprising incubating a penicillin expandase mutant of claim 1 with a substrate for producing G-7-ADCA.

7. The method according to claim 6, wherein the substrate is penicillin G.

* * * * *

SEQUENCE LISTING

```
<160> NUMBER OF SEQ ID NOS: 52

<210> SEQ ID NO 1
<211> LENGTH: 936
<212> TYPE: DNA
<213> ORGANISM: Streptomyces clavuligerus

<400> SEQUENCE: 1
atggatacca cggtaccgac attttctctg gcagaactgc agcagggcct gcatcaggat      60
gaatttcgcc gttgcctgcg cgataaaggt ctgttttatc tgaccgattg tggcctgaca     120
gatacagaac tgaaatctgc taaagacctg gttattgatt tttttgaaca tggcagtgaa     180
gcagaaaaac gtgccgtaac atccccggtg cctactatgc gtcgtggctt tacgggcctg     240
gaatccgaat ctacagcgca gatcacgaac accggctcat attccgatta ttcaatgtgc     300
tatagcatgg gtacagcaga taatctgttt ccgtcaggtg attttgaacg catctggacg     360
cagtattttg atcgccagta taccgccagt cgcgcagttg cacgcgaagt tctgcgcgcc     420
accggtacgg aacctgatgg tggtgtggaa gcttttctgg attgcgaacc actgctgcgc     480
tttcgctatt ttccgcaggt ccctgaacat cgtagcgcag aagaacagcc gctgcgtatg     540
gcacctcatt atgatctgtc tatggtaacg ctgatccagc agacgccttg tgcaaacggc     600
tttgtgtcac tgcaggccga agtcggcggc gcctttaccg atctgccttt agcccagat    660 gccgttctgg ttttttgtgg tgcaatcgcg accctggtga caggtggcca ggtgaaagcg     720
ccacgtcatc atgtggcagc gccgcgtcgc gatcagatcg caggttcaag tcgtacaagt     780
tccgtttttt ttctgcgtcc gaatgcagat tttacctttt ctgtgccgct ggcccgcgaa     840
tgcggctttg atgtatccct ggatggcgaa actgcaacat tcaggattg gattggcggt      900 aactatgtga acattcgtcg tacgagtaaa gcttaa                             936

<210> SEQ ID NO 2
<211> LENGTH: 311
<212> TYPE: PRT
<213> ORGANISM: Streptomyces clavuligerus

<400> SEQUENCE: 2

Met Asp Thr Thr Val Pro Thr Phe Ser Leu Ala Glu Leu Gln Gln Gly
1               5                   10                  15
```

-continued

```
Leu His Gln Asp Glu Phe Arg Arg Cys Leu Arg Asp Lys Gly Leu Phe
            20                  25                  30

Tyr Leu Thr Asp Cys Gly Leu Thr Asp Thr Glu Leu Lys Ser Ala Lys
        35                  40                  45

Asp Leu Val Ile Asp Phe Phe Glu His Gly Ser Glu Ala Glu Lys Arg
50                  55                  60

Ala Val Thr Ser Pro Val Pro Thr Met Arg Arg Gly Phe Thr Gly Leu
65                  70                  75                  80

Glu Ser Glu Ser Thr Ala Gln Ile Thr Asn Thr Gly Ser Tyr Ser Asp
                85                  90                  95

Tyr Ser Met Cys Tyr Ser Met Gly Thr Ala Asp Asn Leu Phe Pro Ser
            100                 105                 110

Gly Asp Phe Glu Arg Ile Trp Thr Gln Tyr Phe Asp Arg Gln Tyr Thr
        115                 120                 125

Ala Ser Arg Ala Val Ala Arg Glu Val Leu Arg Ala Thr Gly Thr Glu
130                 135                 140

Pro Asp Gly Gly Val Glu Ala Phe Leu Asp Cys Glu Pro Leu Leu Arg
145                 150                 155                 160

Phe Arg Tyr Phe Pro Gln Val Pro Glu His Arg Ser Ala Glu Glu Gln
                165                 170                 175

Pro Leu Arg Met Ala Pro His Tyr Asp Leu Ser Met Val Thr Leu Ile
            180                 185                 190

Gln Gln Thr Pro Cys Ala Asn Gly Phe Val Ser Leu Gln Ala Glu Val
        195                 200                 205

Gly Gly Ala Phe Thr Asp Leu Pro Tyr Arg Pro Asp Ala Val Leu Val
210                 215                 220

Phe Cys Gly Ala Ile Ala Thr Leu Val Thr Gly Gly Gln Val Lys Ala
225                 230                 235                 240

Pro Arg His His Val Ala Ala Pro Arg Arg Asp Gln Ile Ala Gly Ser
                245                 250                 255

Ser Arg Thr Ser Ser Val Phe Phe Leu Arg Pro Asn Ala Asp Phe Thr
            260                 265                 270

Phe Ser Val Pro Leu Ala Arg Glu Cys Gly Phe Asp Val Ser Leu Asp
        275                 280                 285

Gly Glu Thr Ala Thr Phe Gln Asp Trp Ile Gly Gly Asn Tyr Val Asn
290                 295                 300

Ile Arg Arg Thr Ser Lys Ala
305                 310

<210> SEQ ID NO 3
<211> LENGTH: 936
<212> TYPE: DNA
<213> ORGANISM: Artificial Sequence
<220> FEATURE:
<223> OTHER INFORMATION: penicillin expandase mutant
<220> FEATURE:
<221> NAME/KEY: misc_feature
<222> LOCATION: (124)..(126)
<223> OTHER INFORMATION: n is a c g or t
<220> FEATURE:
<221> NAME/KEY: misc_feature
<222> LOCATION: (376)..(378)
<223> OTHER INFORMATION: n is a c g or t

<400> SEQUENCE: 3
atggatacca cggtaccgac attttctctg gcagaactgc agcagggcct gcatcaggat    60
gaatttcgcc gttgcctgcg cgataaaggt ctgtttttatc tgaccgattg tggcctgaca   120
```

| | |
|---|---|
| gatnnngaac tgaaatctgc taaagacctg gttattgatt tttttgaaca tggcagtgaa | 180 |
| gcagaaaaac gtgccgtaac atccccggtg cctactatgc gtcgtggctt tacgggcctg | 240 |
| gaatccgaat ctacagcgca gatcacgaac accggctcat attccgatta ttcaatgtgc | 300 |
| tatagcatgg gtacagcaga taatctgttt ccgtcaggtg attttgaacg catctggacg | 360 |
| cagtattttg atcgcnnnta taccgccagt cgcgcagttg cacgcgaagt tctgcgcgcc | 420 |
| accggtacgg aacctgatgg tggtgtggaa gcttttctgg attgcgaacc actgctgcgc | 480 |
| tttcgctatt tccgcaggt ccctgaacat cgtagcgcag aagaacagcc gctgcgtatg | 540 |
| gcacctcatt atgatctgtc tatggtaacg ctgatccagc agacgccttg tgcaaacggc | 600 |
| tttgtgtcac tgcaggccga agtcggcggc gcctttaccg atctgcctta cgcccagat | 660 |
| gccgttctgg ttttttgtgg tgcaatcgcg accctggtga caggtggcca ggtgaaagcg | 720 |
| ccacgtcatc atgtggcagc gccgcgtcgc gatcagatcg caggttcaag tcgtacaagt | 780 |
| tccgtttttt ttctgcgtcc gaatgcagat tttaccttt ctgtgccgct ggcccgcgaa | 840 |
| tgcggctttg atgtatccct ggatggcgaa actgcaacat tcaggattg gattggcggt | 900 |
| aactatgtga acattcgtcg tacgagtaaa gcttaa | 936 |

<210> SEQ ID NO 4
<211> LENGTH: 311
<212> TYPE: PRT
<213> ORGANISM: Artificial Sequence
<220> FEATURE:
<223> OTHER INFORMATION: penicillin expandase mutant
<220> FEATURE:
<221> NAME/KEY: misc_feature
<222> LOCATION: (42)..(42)
<223> OTHER INFORMATION: Xaa is any other natural amino acid except
      threonine
<220> FEATURE:
<221> NAME/KEY: misc_feature
<222> LOCATION: (126)..(126)
<223> OTHER INFORMATION: Xaa is any other natural amino acid except
      glutamine

<400> SEQUENCE: 4

Met Asp Thr Thr Val Pro Thr Phe Ser Leu Ala Glu Leu Gln Gln Gly
1               5                   10                  15

Leu His Gln Asp Glu Phe Arg Arg Cys Leu Arg Asp Lys Gly Leu Phe
                20                  25                  30

Tyr Leu Thr Asp Cys Gly Leu Thr Asp Xaa Glu Leu Lys Ser Ala Lys
            35                  40                  45

Asp Leu Val Ile Asp Phe Phe Glu His Gly Ser Glu Ala Glu Lys Arg
50                  55                  60

Ala Val Thr Ser Pro Val Pro Thr Met Arg Arg Gly Phe Thr Gly Leu
65                  70                  75                  80

Glu Ser Glu Ser Thr Ala Gln Ile Thr Asn Thr Gly Ser Tyr Ser Asp
                85                  90                  95

Tyr Ser Met Cys Tyr Ser Met Gly Thr Ala Asp Asn Leu Phe Pro Ser
            100                 105                 110

Gly Asp Phe Glu Arg Ile Trp Thr Gln Tyr Phe Asp Arg Xaa Tyr Thr
        115                 120                 125

Ala Ser Arg Ala Val Ala Arg Glu Val Leu Arg Ala Thr Gly Thr Glu
    130                 135                 140

Pro Asp Gly Gly Val Glu Ala Phe Leu Asp Cys Glu Pro Leu Leu Arg
145                 150                 155                 160

Phe Arg Tyr Phe Pro Gln Val Pro Glu His Arg Ser Ala Glu Glu Gln

```
                165                 170                 175
Pro Leu Arg Met Ala Pro His Tyr Asp Leu Ser Met Val Thr Leu Ile
            180                 185                 190

Gln Gln Thr Pro Cys Ala Asn Gly Phe Val Ser Leu Gln Ala Glu Val
        195                 200                 205

Gly Gly Ala Phe Thr Asp Leu Pro Tyr Arg Pro Asp Ala Val Leu Val
    210                 215                 220

Phe Cys Gly Ala Ile Ala Thr Leu Val Thr Gly Gly Gln Val Lys Ala
225                 230                 235                 240

Pro Arg His His Val Ala Ala Pro Arg Arg Asp Gln Ile Ala Gly Ser
            245                 250                 255

Ser Arg Thr Ser Ser Val Phe Phe Leu Arg Pro Asn Ala Asp Phe Thr
        260                 265                 270

Phe Ser Val Pro Leu Ala Arg Glu Cys Gly Phe Asp Val Ser Leu Asp
    275                 280                 285

Gly Glu Thr Ala Thr Phe Gln Asp Trp Ile Gly Gly Asn Tyr Val Asn
290                 295                 300

Ile Arg Arg Thr Ser Lys Ala
305                 310

<210> SEQ ID NO 5
<211> LENGTH: 311
<212> TYPE: PRT
<213> ORGANISM: Artificial Sequence
<220> FEATURE:
<223> OTHER INFORMATION: SC-T42C mutant

<400> SEQUENCE: 5

Met Asp Thr Thr Val Pro Thr Phe Ser Leu Ala Glu Leu Gln Gln Gly
1               5                   10                  15

Leu His Gln Asp Glu Phe Arg Arg Cys Leu Arg Asp Lys Gly Leu Phe
            20                  25                  30

Tyr Leu Thr Asp Cys Gly Leu Thr Asp Cys Glu Leu Lys Ser Ala Lys
        35                  40                  45

Asp Leu Val Ile Asp Phe Phe Glu His Gly Ser Glu Ala Glu Lys Arg
    50                  55                  60

Ala Val Thr Ser Pro Val Pro Thr Met Arg Arg Gly Phe Thr Gly Leu
65                  70                  75                  80

Glu Ser Glu Ser Thr Ala Gln Ile Thr Asn Thr Gly Ser Tyr Ser Asp
            85                  90                  95

Tyr Ser Met Cys Tyr Ser Met Gly Thr Ala Asp Asn Leu Phe Pro Ser
        100                 105                 110

Gly Asp Phe Glu Arg Ile Trp Thr Gln Tyr Phe Asp Arg Gln Tyr Thr
    115                 120                 125

Ala Ser Arg Ala Val Ala Arg Glu Val Leu Arg Ala Thr Gly Thr Glu
130                 135                 140

Pro Asp Gly Gly Val Glu Ala Phe Leu Asp Cys Glu Pro Leu Leu Arg
            145                 150                 155                 160

Phe Arg Tyr Phe Pro Gln Val Pro Glu His Arg Ser Ala Glu Glu Gln
        165                 170                 175

Pro Leu Arg Met Ala Pro His Tyr Asp Leu Ser Met Val Thr Leu Ile
    180                 185                 190

Gln Gln Thr Pro Cys Ala Asn Gly Phe Val Ser Leu Gln Ala Glu Val
195                 200                 205

Gly Gly Ala Phe Thr Asp Leu Pro Tyr Arg Pro Asp Ala Val Leu Val
```

```
              210                 215                 220
Phe Cys Gly Ala Ile Ala Thr Leu Val Thr Gly Gly Gln Val Lys Ala
225                 230                 235                 240

Pro Arg His His Val Ala Ala Pro Arg Arg Asp Gln Ile Ala Gly Ser
                245                 250                 255

Ser Arg Thr Ser Ser Val Phe Phe Leu Arg Pro Asn Ala Asp Phe Thr
                260                 265                 270

Phe Ser Val Pro Leu Ala Arg Glu Cys Gly Phe Asp Val Ser Leu Asp
                275                 280                 285

Gly Glu Thr Ala Thr Phe Gln Asp Trp Ile Gly Gly Asn Tyr Val Asn
290                 295                 300

Ile Arg Arg Thr Ser Lys Ala
305                 310

<210> SEQ ID NO 6
<211> LENGTH: 311
<212> TYPE: PRT
<213> ORGANISM: Artificial Sequence
<220> FEATURE:
<223> OTHER INFORMATION: SC-T42D mutant

<400> SEQUENCE: 6

Met Asp Thr Thr Val Pro Thr Phe Ser Leu Ala Glu Leu Gln Gln Gly
1               5                   10                  15

Leu His Gln Asp Glu Phe Arg Arg Cys Leu Arg Asp Lys Gly Leu Phe
                20                  25                  30

Tyr Leu Thr Asp Cys Gly Leu Thr Asp Asp Glu Leu Lys Ser Ala Lys
            35                  40                  45

Asp Leu Val Ile Asp Phe Phe Glu His Gly Ser Glu Ala Glu Lys Arg
        50                  55                  60

Ala Val Thr Ser Pro Val Pro Thr Met Arg Arg Gly Phe Thr Gly Leu
65                  70                  75                  80

Glu Ser Glu Ser Thr Ala Gln Ile Thr Asn Thr Gly Ser Tyr Ser Asp
                85                  90                  95

Tyr Ser Met Cys Tyr Ser Met Gly Thr Ala Asp Asn Leu Phe Pro Ser
                100                 105                 110

Gly Asp Phe Glu Arg Ile Trp Thr Gln Tyr Phe Asp Arg Gln Tyr Thr
            115                 120                 125

Ala Ser Arg Ala Val Ala Arg Glu Val Leu Arg Ala Thr Gly Thr Glu
        130                 135                 140

Pro Asp Gly Gly Val Glu Ala Phe Leu Asp Cys Glu Pro Leu Leu Arg
145                 150                 155                 160

Phe Arg Tyr Phe Pro Gln Val Pro Glu His Arg Ser Ala Glu Glu Gln
                165                 170                 175

Pro Leu Arg Met Ala Pro His Tyr Asp Leu Ser Met Val Thr Leu Ile
                180                 185                 190

Gln Gln Thr Pro Cys Ala Asn Gly Phe Val Ser Leu Gln Ala Glu Val
            195                 200                 205

Gly Gly Ala Phe Thr Asp Leu Pro Tyr Arg Pro Asp Ala Val Leu Val
        210                 215                 220

Phe Cys Gly Ala Ile Ala Thr Leu Val Thr Gly Gly Gln Val Lys Ala
225                 230                 235                 240

Pro Arg His His Val Ala Ala Pro Arg Arg Asp Gln Ile Ala Gly Ser
                245                 250                 255

Ser Arg Thr Ser Ser Val Phe Phe Leu Arg Pro Asn Ala Asp Phe Thr
```

```
                260                 265                 270
Phe Ser Val Pro Leu Ala Arg Glu Cys Gly Phe Asp Val Ser Leu Asp
            275                 280                 285
Gly Glu Thr Ala Thr Phe Gln Asp Trp Ile Gly Gly Asn Tyr Val Asn
        290                 295                 300
Ile Arg Arg Thr Ser Lys Ala
305                 310

<210> SEQ ID NO 7
<211> LENGTH: 311
<212> TYPE: PRT
<213> ORGANISM: artificial sequence
<220> FEATURE:
<223> OTHER INFORMATION: SC-T42E mutant

<400> SEQUENCE: 7

Met Asp Thr Thr Val Pro Thr Phe Ser Leu Ala Glu Leu Gln Gln Gly
1               5                   10                  15
Leu His Gln Asp Glu Phe Arg Arg Cys Leu Arg Asp Lys Gly Leu Phe
            20                  25                  30
Tyr Leu Thr Asp Cys Gly Leu Thr Asp Glu Glu Leu Lys Ser Ala Lys
        35                  40                  45
Asp Leu Val Ile Asp Phe Phe Glu His Gly Ser Glu Ala Glu Lys Arg
    50                  55                  60
Ala Val Thr Ser Pro Val Pro Thr Met Arg Arg Gly Phe Thr Gly Leu
65                  70                  75                  80
Glu Ser Glu Ser Thr Ala Gln Ile Thr Asn Thr Gly Ser Tyr Ser Asp
                85                  90                  95
Tyr Ser Met Cys Tyr Ser Met Gly Thr Ala Asp Asn Leu Phe Pro Ser
            100                 105                 110
Gly Asp Phe Glu Arg Ile Trp Thr Gln Tyr Phe Asp Arg Gln Tyr Thr
        115                 120                 125
Ala Ser Arg Ala Val Ala Arg Glu Val Leu Arg Ala Thr Gly Thr Glu
    130                 135                 140
Pro Asp Gly Gly Val Glu Ala Phe Leu Asp Cys Glu Pro Leu Leu Arg
145                 150                 155                 160
Phe Arg Tyr Phe Pro Gln Val Pro Glu His Arg Ser Ala Glu Glu Gln
                165                 170                 175
Pro Leu Arg Met Ala Pro His Tyr Asp Leu Ser Met Val Thr Leu Ile
            180                 185                 190
Gln Gln Thr Pro Cys Ala Asn Gly Phe Val Ser Leu Gln Ala Glu Val
        195                 200                 205
Gly Gly Ala Phe Thr Asp Leu Pro Tyr Arg Pro Asp Ala Val Leu Val
    210                 215                 220
Phe Cys Gly Ala Ile Ala Thr Leu Val Thr Gly Gly Gln Val Lys Ala
225                 230                 235                 240
Pro Arg His His Val Ala Ala Pro Arg Arg Asp Gln Ile Ala Gly Ser
                245                 250                 255
Ser Arg Thr Ser Ser Val Phe Phe Leu Arg Pro Asn Ala Asp Phe Thr
            260                 265                 270
Phe Ser Val Pro Leu Ala Arg Glu Cys Gly Phe Asp Val Ser Leu Asp
        275                 280                 285
Gly Glu Thr Ala Thr Phe Gln Asp Trp Ile Gly Gly Asn Tyr Val Asn
    290                 295                 300
Ile Arg Arg Thr Ser Lys Ala
305                 310
```

<210> SEQ ID NO 8
<211> LENGTH: 311
<212> TYPE: PRT
<213> ORGANISM: Artificial Sequence
<220> FEATURE:
<223> OTHER INFORMATION: SC-T42M mutant

<400> SEQUENCE: 8

```
Met Asp Thr Thr Val Pro Thr Phe Ser Leu Ala Glu Leu Gln Gln Gly
1               5                   10                  15

Leu His Gln Asp Glu Phe Arg Arg Cys Leu Arg Asp Lys Gly Leu Phe
            20                  25                  30

Tyr Leu Thr Asp Cys Gly Leu Thr Asp Met Glu Leu Lys Ser Ala Lys
        35                  40                  45

Asp Leu Val Ile Asp Phe Phe Glu His Gly Ser Glu Ala Glu Lys Arg
    50                  55                  60

Ala Val Thr Ser Pro Val Pro Thr Met Arg Arg Gly Phe Thr Gly Leu
65                  70                  75                  80

Glu Ser Glu Ser Thr Ala Gln Ile Thr Asn Thr Gly Ser Tyr Ser Asp
                85                  90                  95

Tyr Ser Met Cys Tyr Ser Met Gly Thr Ala Asp Asn Leu Phe Pro Ser
            100                 105                 110

Gly Asp Phe Glu Arg Ile Trp Thr Gln Tyr Phe Asp Arg Gln Tyr Thr
        115                 120                 125

Ala Ser Arg Ala Val Ala Arg Glu Val Leu Arg Ala Thr Gly Thr Glu
    130                 135                 140

Pro Asp Gly Gly Val Glu Ala Phe Leu Asp Cys Glu Pro Leu Leu Arg
145                 150                 155                 160

Phe Arg Tyr Phe Pro Gln Val Pro Glu His Arg Ser Ala Glu Glu Gln
                165                 170                 175

Pro Leu Arg Met Ala Pro His Tyr Asp Leu Ser Met Val Thr Leu Ile
            180                 185                 190

Gln Gln Thr Pro Cys Ala Asn Gly Phe Val Ser Leu Gln Ala Glu Val
        195                 200                 205

Gly Gly Ala Phe Thr Asp Leu Pro Tyr Arg Pro Asp Ala Val Leu Val
    210                 215                 220

Phe Cys Gly Ala Ile Ala Thr Leu Val Thr Gly Gly Gln Val Lys Ala
225                 230                 235                 240

Pro Arg His His Val Ala Ala Pro Arg Arg Asp Gln Ile Ala Gly Ser
                245                 250                 255

Ser Arg Thr Ser Ser Val Phe Phe Leu Arg Pro Asn Ala Asp Phe Thr
            260                 265                 270

Phe Ser Val Pro Leu Ala Arg Glu Cys Gly Phe Asp Val Ser Leu Asp
        275                 280                 285

Gly Glu Thr Ala Thr Phe Gln Asp Trp Ile Gly Gly Asn Tyr Val Asn
    290                 295                 300

Ile Arg Arg Thr Ser Lys Ala
305                 310
```

<210> SEQ ID NO 9
<211> LENGTH: 311
<212> TYPE: PRT
<213> ORGANISM: Artificial Sequence
<220> FEATURE:
<223> OTHER INFORMATION: SC-T42P mutant

<400> SEQUENCE: 9

Met Asp Thr Thr Val Pro Thr Phe Ser Leu Ala Glu Leu Gln Gln Gly
1               5                   10                  15

Leu His Gln Asp Glu Phe Arg Arg Cys Leu Arg Asp Lys Gly Leu Phe
            20                  25                  30

Tyr Leu Thr Asp Cys Gly Leu Thr Asp Pro Glu Leu Lys Ser Ala Lys
        35                  40                  45

Asp Leu Val Ile Asp Phe Phe Glu His Gly Ser Glu Ala Glu Lys Arg
    50                  55                  60

Ala Val Thr Ser Pro Val Pro Thr Met Arg Arg Gly Phe Thr Gly Leu
65                  70                  75                  80

Glu Ser Glu Ser Thr Ala Gln Ile Thr Asn Thr Gly Ser Tyr Ser Asp
                85                  90                  95

Tyr Ser Met Cys Tyr Ser Met Gly Thr Ala Asp Asn Leu Phe Pro Ser
            100                 105                 110

Gly Asp Phe Glu Arg Ile Trp Thr Gln Tyr Phe Asp Arg Gln Tyr Thr
        115                 120                 125

Ala Ser Arg Ala Val Ala Arg Glu Val Leu Arg Ala Thr Gly Thr Glu
    130                 135                 140

Pro Asp Gly Gly Val Glu Ala Phe Leu Asp Cys Glu Pro Leu Leu Arg
145                 150                 155                 160

Phe Arg Tyr Phe Pro Gln Val Pro Glu His Arg Ser Ala Glu Glu Gln
                165                 170                 175

Pro Leu Arg Met Ala Pro His Tyr Asp Leu Ser Met Val Thr Leu Ile
            180                 185                 190

Gln Gln Thr Pro Cys Ala Asn Gly Phe Val Ser Leu Gln Ala Glu Val
        195                 200                 205

Gly Gly Ala Phe Thr Asp Leu Pro Tyr Arg Pro Asp Ala Val Leu Val
    210                 215                 220

Phe Cys Gly Ala Ile Ala Thr Leu Val Thr Gly Gly Gln Val Lys Ala
225                 230                 235                 240

Pro Arg His His Val Ala Ala Pro Arg Arg Asp Gln Ile Ala Gly Ser
                245                 250                 255

Ser Arg Thr Ser Ser Val Phe Phe Leu Arg Pro Asn Ala Asp Phe Thr
            260                 265                 270

Phe Ser Val Pro Leu Ala Arg Glu Cys Gly Phe Asp Val Ser Leu Asp
        275                 280                 285

Gly Glu Thr Ala Thr Phe Gln Asp Trp Ile Gly Gly Asn Tyr Val Asn
    290                 295                 300

Ile Arg Arg Thr Ser Lys Ala
305                 310

<210> SEQ ID NO 10
<211> LENGTH: 311
<212> TYPE: PRT
<213> ORGANISM: Artificial Sequence
<220> FEATURE:
<223> OTHER INFORMATION: SC-T42Q mutant

<400> SEQUENCE: 10

Met Asp Thr Thr Val Pro Thr Phe Ser Leu Ala Glu Leu Gln Gln Gly
1               5                   10                  15

Leu His Gln Asp Glu Phe Arg Arg Cys Leu Arg Asp Lys Gly Leu Phe
            20                  25                  30

-continued

```
Tyr Leu Thr Asp Cys Gly Leu Thr Asp Gln Glu Leu Lys Ser Ala Lys
             35                  40                  45

Asp Leu Val Ile Asp Phe Phe Glu His Gly Ser Glu Ala Glu Lys Arg
 50                  55                  60

Ala Val Thr Ser Pro Val Pro Thr Met Arg Arg Gly Phe Thr Gly Leu
 65                  70                  75                  80

Glu Ser Glu Ser Thr Ala Gln Ile Thr Asn Thr Gly Ser Tyr Ser Asp
                 85                  90                  95

Tyr Ser Met Cys Tyr Ser Met Gly Thr Ala Asp Asn Leu Phe Pro Ser
            100                 105                 110

Gly Asp Phe Glu Arg Ile Trp Thr Gln Tyr Phe Asp Arg Gln Tyr Thr
        115                 120                 125

Ala Ser Arg Ala Val Ala Arg Glu Val Leu Arg Ala Thr Gly Thr Glu
    130                 135                 140

Pro Asp Gly Gly Val Glu Ala Phe Leu Asp Cys Glu Pro Leu Leu Arg
145                 150                 155                 160

Phe Arg Tyr Phe Pro Gln Val Pro Glu His Arg Ser Ala Glu Glu Gln
                165                 170                 175

Pro Leu Arg Met Ala Pro His Tyr Asp Leu Ser Met Val Thr Leu Ile
            180                 185                 190

Gln Gln Thr Pro Cys Ala Asn Gly Phe Val Ser Leu Gln Ala Glu Val
        195                 200                 205

Gly Gly Ala Phe Thr Asp Leu Pro Tyr Arg Pro Asp Ala Val Leu Val
    210                 215                 220

Phe Cys Gly Ala Ile Ala Thr Leu Val Thr Gly Gly Gln Val Lys Ala
225                 230                 235                 240

Pro Arg His His Val Ala Ala Pro Arg Arg Asp Gln Ile Ala Gly Ser
                245                 250                 255

Ser Arg Thr Ser Ser Val Phe Phe Leu Arg Pro Asn Ala Asp Phe Thr
            260                 265                 270

Phe Ser Val Pro Leu Ala Arg Glu Cys Gly Phe Asp Val Ser Leu Asp
        275                 280                 285

Gly Glu Thr Ala Thr Phe Gln Asp Trp Ile Gly Gly Asn Tyr Val Asn
    290                 295                 300

Ile Arg Arg Thr Ser Lys Ala
305                 310
```

<210> SEQ ID NO 11
<211> LENGTH: 311
<212> TYPE: PRT
<213> ORGANISM: Artificial Sequence
<220> FEATURE:
<223> OTHER INFORMATION: SC-T42R mutant

<400> SEQUENCE: 11

```
Met Asp Thr Thr Val Pro Thr Phe Ser Leu Ala Glu Leu Gln Gln Gly
 1               5                  10                  15

Leu His Gln Asp Glu Phe Arg Arg Cys Leu Arg Asp Lys Gly Leu Phe
             20                  25                  30

Tyr Leu Thr Asp Cys Gly Leu Thr Asp Arg Glu Leu Lys Ser Ala Lys
             35                  40                  45

Asp Leu Val Ile Asp Phe Phe Glu His Gly Ser Glu Ala Glu Lys Arg
 50                  55                  60

Ala Val Thr Ser Pro Val Pro Thr Met Arg Arg Gly Phe Thr Gly Leu
 65                  70                  75                  80
```

```
Glu Ser Glu Ser Thr Ala Gln Ile Thr Asn Thr Gly Ser Tyr Ser Asp
                85                  90                  95

Tyr Ser Met Cys Tyr Ser Met Gly Thr Ala Asp Asn Leu Phe Pro Ser
            100                 105                 110

Gly Asp Phe Glu Arg Ile Trp Thr Gln Tyr Phe Asp Arg Gln Tyr Thr
        115                 120                 125

Ala Ser Arg Ala Val Ala Arg Glu Val Leu Arg Ala Thr Gly Thr Glu
130                 135                 140

Pro Asp Gly Gly Val Glu Ala Phe Leu Asp Cys Glu Pro Leu Leu Arg
145                 150                 155                 160

Phe Arg Tyr Phe Pro Gln Val Pro Glu His Arg Ser Ala Glu Glu Gln
                165                 170                 175

Pro Leu Arg Met Ala Pro His Tyr Asp Leu Ser Met Val Thr Leu Ile
            180                 185                 190

Gln Gln Thr Pro Cys Ala Asn Gly Phe Val Ser Leu Gln Ala Glu Val
        195                 200                 205

Gly Gly Ala Phe Thr Asp Leu Pro Tyr Arg Pro Asp Ala Val Leu Val
210                 215                 220

Phe Cys Gly Ala Ile Ala Thr Leu Val Thr Gly Gly Gln Val Lys Ala
225                 230                 235                 240

Pro Arg His His Val Ala Ala Pro Arg Arg Asp Gln Ile Ala Gly Ser
                245                 250                 255

Ser Arg Thr Ser Ser Val Phe Phe Leu Arg Pro Asn Ala Asp Phe Thr
            260                 265                 270

Phe Ser Val Pro Leu Ala Arg Glu Cys Gly Phe Asp Val Ser Leu Asp
        275                 280                 285

Gly Glu Thr Ala Thr Phe Gln Asp Trp Ile Gly Gly Asn Tyr Val Asn
290                 295                 300

Ile Arg Arg Thr Ser Lys Ala
305                 310

<210> SEQ ID NO 12
<211> LENGTH: 311
<212> TYPE: PRT
<213> ORGANISM: Artificial Sequence
<220> FEATURE:
<223> OTHER INFORMATION: SC-Q126A mutant

<400> SEQUENCE: 12

Met Asp Thr Thr Val Pro Thr Phe Ser Leu Ala Glu Leu Gln Gln Gly
1               5                   10                  15

Leu His Gln Asp Glu Phe Arg Arg Cys Leu Arg Asp Lys Gly Leu Phe
            20                  25                  30

Tyr Leu Thr Asp Cys Gly Leu Thr Asp Thr Glu Leu Lys Ser Ala Lys
        35                  40                  45

Asp Leu Val Ile Asp Phe Phe Glu His Gly Ser Glu Ala Glu Lys Arg
50                  55                  60

Ala Val Thr Ser Pro Val Pro Thr Met Arg Arg Gly Phe Thr Gly Leu
65                  70                  75                  80

Glu Ser Glu Ser Thr Ala Gln Ile Thr Asn Thr Gly Ser Tyr Ser Asp
                85                  90                  95

Tyr Ser Met Cys Tyr Ser Met Gly Thr Ala Asp Asn Leu Phe Pro Ser
            100                 105                 110

Gly Asp Phe Glu Arg Ile Trp Thr Gln Tyr Phe Asp Arg Ala Tyr Thr
        115                 120                 125
```

```
Ala Ser Arg Ala Val Ala Arg Glu Val Leu Arg Ala Thr Gly Thr Glu
        130                 135                 140

Pro Asp Gly Gly Val Glu Ala Phe Leu Asp Cys Glu Pro Leu Leu Arg
145                 150                 155                 160

Phe Arg Tyr Phe Pro Gln Val Pro Glu His Arg Ser Ala Glu Glu Gln
                165                 170                 175

Pro Leu Arg Met Ala Pro His Tyr Asp Leu Ser Met Val Thr Leu Ile
        180                 185                 190

Gln Gln Thr Pro Cys Ala Asn Gly Phe Val Ser Leu Gln Ala Glu Val
            195                 200                 205

Gly Gly Ala Phe Thr Asp Leu Pro Tyr Arg Pro Asp Ala Val Leu Val
    210                 215                 220

Phe Cys Gly Ala Ile Ala Thr Leu Val Thr Gly Gly Gln Val Lys Ala
225                 230                 235                 240

Pro Arg His His Val Ala Ala Pro Arg Arg Asp Gln Ile Ala Gly Ser
                245                 250                 255

Ser Arg Thr Ser Ser Val Phe Phe Leu Arg Pro Asn Ala Asp Phe Thr
        260                 265                 270

Phe Ser Val Pro Leu Ala Arg Glu Cys Gly Phe Asp Val Ser Leu Asp
        275                 280                 285

Gly Glu Thr Ala Thr Phe Gln Asp Trp Ile Gly Gly Asn Tyr Val Asn
    290                 295                 300

Ile Arg Arg Thr Ser Lys Ala
305                 310

<210> SEQ ID NO 13
<211> LENGTH: 311
<212> TYPE: PRT
<213> ORGANISM: Artificial Sequence
<220> FEATURE:
<223> OTHER INFORMATION: SC-Q126F mutant

<400> SEQUENCE: 13

Met Asp Thr Thr Val Pro Thr Phe Ser Leu Ala Glu Leu Gln Gln Gly
1               5                   10                  15

Leu His Gln Asp Glu Phe Arg Arg Cys Leu Arg Asp Lys Gly Leu Phe
            20                  25                  30

Tyr Leu Thr Asp Cys Gly Leu Thr Asp Thr Glu Leu Lys Ser Ala Lys
        35                  40                  45

Asp Leu Val Ile Asp Phe Phe Glu His Gly Ser Glu Ala Glu Lys Arg
    50                  55                  60

Ala Val Thr Ser Pro Val Pro Thr Met Arg Arg Gly Phe Thr Gly Leu
65                  70                  75                  80

Glu Ser Glu Ser Thr Ala Gln Ile Thr Asn Thr Gly Ser Tyr Ser Asp
            85                  90                  95

Tyr Ser Met Cys Tyr Ser Met Gly Thr Ala Asp Asn Leu Phe Pro Ser
        100                 105                 110

Gly Asp Phe Glu Arg Ile Trp Thr Gln Tyr Phe Asp Arg Phe Tyr Thr
    115                 120                 125

Ala Ser Arg Ala Val Ala Arg Glu Val Leu Arg Ala Thr Gly Thr Glu
        130                 135                 140

Pro Asp Gly Gly Val Glu Ala Phe Leu Asp Cys Glu Pro Leu Leu Arg
145                 150                 155                 160

Phe Arg Tyr Phe Pro Gln Val Pro Glu His Arg Ser Ala Glu Glu Gln
                165                 170                 175
```

```
Pro Leu Arg Met Ala Pro His Tyr Asp Leu Ser Met Val Thr Leu Ile
            180                 185                 190

Gln Gln Thr Pro Cys Ala Asn Gly Phe Val Ser Leu Gln Ala Glu Val
        195                 200                 205

Gly Gly Ala Phe Thr Asp Leu Pro Tyr Arg Pro Asp Ala Val Leu Val
    210                 215                 220

Phe Cys Gly Ala Ile Ala Thr Leu Val Thr Gly Gly Gln Val Lys Ala
225                 230                 235                 240

Pro Arg His His Val Ala Ala Pro Arg Arg Asp Gln Ile Ala Gly Ser
            245                 250                 255

Ser Arg Thr Ser Ser Val Phe Phe Leu Arg Pro Asn Ala Asp Phe Thr
        260                 265                 270

Phe Ser Val Pro Leu Ala Arg Glu Cys Gly Phe Asp Val Ser Leu Asp
    275                 280                 285

Gly Glu Thr Ala Thr Phe Gln Asp Trp Ile Gly Gly Asn Tyr Val Asn
    290                 295                 300

Ile Arg Arg Thr Ser Lys Ala
305                 310
```

<210> SEQ ID NO 14
<211> LENGTH: 311
<212> TYPE: PRT
<213> ORGANISM: Artificial Sequence
<220> FEATURE:
<223> OTHER INFORMATION: SC-Q126I mutant

<400> SEQUENCE: 14

```
Met Asp Thr Thr Val Pro Thr Phe Ser Leu Ala Glu Leu Gln Gln Gly
1               5                   10                  15

Leu His Gln Asp Glu Phe Arg Arg Cys Leu Arg Asp Lys Gly Leu Phe
            20                  25                  30

Tyr Leu Thr Asp Cys Gly Leu Thr Asp Thr Glu Leu Lys Ser Ala Lys
        35                  40                  45

Asp Leu Val Ile Asp Phe Phe Glu His Gly Ser Glu Ala Glu Lys Arg
    50                  55                  60

Ala Val Thr Ser Pro Val Pro Thr Met Arg Arg Gly Phe Thr Gly Leu
65                  70                  75                  80

Glu Ser Glu Ser Thr Ala Gln Ile Thr Asn Thr Gly Ser Tyr Ser Asp
            85                  90                  95

Tyr Ser Met Cys Tyr Ser Met Gly Thr Ala Asp Asn Leu Phe Pro Ser
        100                 105                 110

Gly Asp Phe Glu Arg Ile Trp Thr Gln Tyr Phe Asp Arg Ile Tyr Thr
    115                 120                 125

Ala Ser Arg Ala Val Ala Arg Glu Val Leu Arg Ala Thr Gly Thr Glu
    130                 135                 140

Pro Asp Gly Gly Val Glu Ala Phe Leu Asp Cys Glu Pro Leu Leu Arg
145                 150                 155                 160

Phe Arg Tyr Phe Pro Gln Val Pro Glu His Arg Ser Ala Glu Glu Gln
            165                 170                 175

Pro Leu Arg Met Ala Pro His Tyr Asp Leu Ser Met Val Thr Leu Ile
            180                 185                 190

Gln Gln Thr Pro Cys Ala Asn Gly Phe Val Ser Leu Gln Ala Glu Val
        195                 200                 205

Gly Gly Ala Phe Thr Asp Leu Pro Tyr Arg Pro Asp Ala Val Leu Val
    210                 215                 220
```

```
Phe Cys Gly Ala Ile Ala Thr Leu Val Thr Gly Gly Gln Val Lys Ala
225                 230                 235                 240

Pro Arg His His Val Ala Ala Pro Arg Arg Asp Gln Ile Ala Gly Ser
                245                 250                 255

Ser Arg Thr Ser Ser Val Phe Phe Leu Arg Pro Asn Ala Asp Phe Thr
            260                 265                 270

Phe Ser Val Pro Leu Ala Arg Glu Cys Gly Phe Asp Val Ser Leu Asp
        275                 280                 285

Gly Glu Thr Ala Thr Phe Gln Asp Trp Ile Gly Gly Asn Tyr Val Asn
290                 295                 300

Ile Arg Arg Thr Ser Lys Ala
305                 310
```

<210> SEQ ID NO 15
<211> LENGTH: 311
<212> TYPE: PRT
<213> ORGANISM: Artificial Sequence
<220> FEATURE:
<223> OTHER INFORMATION: SC-Q126L mutant

<400> SEQUENCE: 15

```
Met Asp Thr Thr Val Pro Thr Phe Ser Leu Ala Glu Leu Gln Gln Gly
1               5                   10                  15

Leu His Gln Asp Glu Phe Arg Arg Cys Leu Arg Asp Lys Gly Leu Phe
                20                  25                  30

Tyr Leu Thr Asp Cys Gly Leu Thr Asp Thr Glu Leu Lys Ser Ala Lys
            35                  40                  45

Asp Leu Val Ile Asp Phe Phe Glu His Gly Ser Glu Ala Glu Lys Arg
        50                  55                  60

Ala Val Thr Ser Pro Val Pro Thr Met Arg Arg Gly Phe Thr Gly Leu
65                  70                  75                  80

Glu Ser Glu Ser Thr Ala Gln Ile Thr Asn Thr Gly Ser Tyr Ser Asp
                85                  90                  95

Tyr Ser Met Cys Tyr Ser Met Gly Thr Ala Asp Asn Leu Phe Pro Ser
            100                 105                 110

Gly Asp Phe Glu Arg Ile Trp Thr Gln Tyr Phe Asp Arg Leu Tyr Thr
        115                 120                 125

Ala Ser Arg Ala Val Ala Arg Glu Val Leu Arg Ala Thr Gly Thr Glu
130                 135                 140

Pro Asp Gly Gly Val Glu Ala Phe Leu Asp Cys Glu Pro Leu Leu Arg
145                 150                 155                 160

Phe Arg Tyr Phe Pro Gln Val Pro Glu His Arg Ser Ala Glu Glu Gln
                165                 170                 175

Pro Leu Arg Met Ala Pro His Tyr Asp Leu Ser Met Val Thr Leu Ile
            180                 185                 190

Gln Gln Thr Pro Cys Ala Asn Gly Phe Val Ser Leu Gln Ala Glu Val
        195                 200                 205

Gly Gly Ala Phe Thr Asp Leu Pro Tyr Arg Pro Asp Ala Val Leu Val
210                 215                 220

Phe Cys Gly Ala Ile Ala Thr Leu Val Thr Gly Gly Gln Val Lys Ala
225                 230                 235                 240

Pro Arg His His Val Ala Ala Pro Arg Arg Asp Gln Ile Ala Gly Ser
                245                 250                 255

Ser Arg Thr Ser Ser Val Phe Phe Leu Arg Pro Asn Ala Asp Phe Thr
            260                 265                 270
```

```
Phe Ser Val Pro Leu Ala Arg Glu Cys Gly Phe Asp Val Ser Leu Asp
            275                 280                 285

Gly Glu Thr Ala Thr Phe Gln Asp Trp Ile Gly Gly Asn Tyr Val Asn
        290                 295                 300

Ile Arg Arg Thr Ser Lys Ala
305                 310

<210> SEQ ID NO 16
<211> LENGTH: 311
<212> TYPE: PRT
<213> ORGANISM: Artificial Sequence
<220> FEATURE:
<223> OTHER INFORMATION: SC-Q126M mutant

<400> SEQUENCE: 16

Met Asp Thr Thr Val Pro Thr Phe Ser Leu Ala Glu Leu Gln Gln Gly
1               5                   10                  15

Leu His Gln Asp Glu Phe Arg Arg Cys Leu Arg Asp Lys Gly Leu Phe
            20                  25                  30

Tyr Leu Thr Asp Cys Gly Leu Thr Asp Thr Glu Leu Lys Ser Ala Lys
        35                  40                  45

Asp Leu Val Ile Asp Phe Phe Glu His Gly Ser Glu Ala Glu Lys Arg
    50                  55                  60

Ala Val Thr Ser Pro Val Pro Thr Met Arg Arg Gly Phe Thr Gly Leu
65                  70                  75                  80

Glu Ser Glu Ser Thr Ala Gln Ile Thr Asn Thr Gly Ser Tyr Ser Asp
                85                  90                  95

Tyr Ser Met Cys Tyr Ser Met Gly Thr Ala Asp Asn Leu Phe Pro Ser
            100                 105                 110

Gly Asp Phe Glu Arg Ile Trp Thr Gln Tyr Phe Asp Arg Met Tyr Thr
        115                 120                 125

Ala Ser Arg Ala Val Ala Arg Glu Val Leu Arg Ala Thr Gly Thr Glu
    130                 135                 140

Pro Asp Gly Gly Val Glu Ala Phe Leu Asp Cys Glu Pro Leu Leu Arg
145                 150                 155                 160

Phe Arg Tyr Phe Pro Gln Val Pro Glu His Arg Ser Ala Glu Glu Gln
                165                 170                 175

Pro Leu Arg Met Ala Pro His Tyr Asp Leu Ser Met Val Thr Leu Ile
            180                 185                 190

Gln Gln Thr Pro Cys Ala Asn Gly Phe Val Ser Leu Gln Ala Glu Val
        195                 200                 205

Gly Gly Ala Phe Thr Asp Leu Pro Tyr Arg Pro Asp Ala Val Leu Val
    210                 215                 220

Phe Cys Gly Ala Ile Ala Thr Leu Val Thr Gly Gly Gln Val Lys Ala
225                 230                 235                 240

Pro Arg His His Val Ala Ala Pro Arg Arg Asp Gln Ile Ala Gly Ser
                245                 250                 255

Ser Arg Thr Ser Ser Val Phe Phe Leu Arg Pro Asn Ala Asp Phe Thr
            260                 265                 270

Phe Ser Val Pro Leu Ala Arg Glu Cys Gly Phe Asp Val Ser Leu Asp
        275                 280                 285

Gly Glu Thr Ala Thr Phe Gln Asp Trp Ile Gly Gly Asn Tyr Val Asn
    290                 295                 300

Ile Arg Arg Thr Ser Lys Ala
305                 310
```

<210> SEQ ID NO 17
<211> LENGTH: 311
<212> TYPE: PRT
<213> ORGANISM: Artificial Sequence
<220> FEATURE:
<223> OTHER INFORMATION: SC-Q126N mutant

<400> SEQUENCE: 17

```
Met Asp Thr Thr Val Pro Thr Phe Ser Leu Ala Glu Leu Gln Gln Gly
1               5                   10                  15

Leu His Gln Asp Glu Phe Arg Arg Cys Leu Arg Asp Lys Gly Leu Phe
            20                  25                  30

Tyr Leu Thr Asp Cys Gly Leu Thr Asp Thr Glu Leu Lys Ser Ala Lys
        35                  40                  45

Asp Leu Val Ile Asp Phe Phe Glu His Gly Ser Glu Ala Glu Lys Arg
    50                  55                  60

Ala Val Thr Ser Pro Val Pro Thr Met Arg Arg Gly Phe Thr Gly Leu
65                  70                  75                  80

Glu Ser Glu Ser Thr Ala Gln Ile Thr Asn Thr Gly Ser Tyr Ser Asp
                85                  90                  95

Tyr Ser Met Cys Tyr Ser Met Gly Thr Ala Asp Asn Leu Phe Pro Ser
            100                 105                 110

Gly Asp Phe Glu Arg Ile Trp Thr Gln Tyr Phe Asp Arg Asn Tyr Thr
        115                 120                 125

Ala Ser Arg Ala Val Ala Arg Glu Val Leu Arg Ala Thr Gly Thr Glu
    130                 135                 140

Pro Asp Gly Gly Val Glu Ala Phe Leu Asp Cys Glu Pro Leu Leu Arg
145                 150                 155                 160

Phe Arg Tyr Phe Pro Gln Val Pro Glu His Arg Ser Ala Glu Glu Gln
                165                 170                 175

Pro Leu Arg Met Ala Pro His Tyr Asp Leu Ser Met Val Thr Leu Ile
            180                 185                 190

Gln Gln Thr Pro Cys Ala Asn Gly Phe Val Ser Leu Gln Ala Glu Val
        195                 200                 205

Gly Gly Ala Phe Thr Asp Leu Pro Tyr Arg Pro Asp Ala Val Leu Val
    210                 215                 220

Phe Cys Gly Ala Ile Ala Thr Leu Val Thr Gly Gly Gln Val Lys Ala
225                 230                 235                 240

Pro Arg His His Val Ala Ala Pro Arg Arg Asp Gln Ile Ala Gly Ser
                245                 250                 255

Ser Arg Thr Ser Ser Val Phe Phe Leu Arg Pro Asn Ala Asp Phe Thr
            260                 265                 270

Phe Ser Val Pro Leu Ala Arg Glu Cys Gly Phe Asp Val Ser Leu Asp
        275                 280                 285

Gly Glu Thr Ala Thr Phe Gln Asp Trp Ile Gly Gly Asn Tyr Val Asn
    290                 295                 300

Ile Arg Arg Thr Ser Lys Ala
305                 310
```

<210> SEQ ID NO 18
<211> LENGTH: 311
<212> TYPE: PRT
<213> ORGANISM: Artificial Sequence
<220> FEATURE:
<223> OTHER INFORMATION: SC-Q126W mutant

<400> SEQUENCE: 18

```
Met Asp Thr Thr Val Pro Thr Phe Ser Leu Ala Glu Leu Gln Gln Gly
1               5                   10                  15

Leu His Gln Asp Glu Phe Arg Arg Cys Leu Arg Asp Lys Gly Leu Phe
            20                  25                  30

Tyr Leu Thr Asp Cys Gly Leu Thr Asp Thr Glu Leu Lys Ser Ala Lys
        35                  40                  45

Asp Leu Val Ile Asp Phe Phe Glu His Gly Ser Glu Ala Glu Lys Arg
50                  55                  60

Ala Val Thr Ser Pro Val Pro Thr Met Arg Arg Gly Phe Thr Gly Leu
65                  70                  75                  80

Glu Ser Glu Ser Thr Ala Gln Ile Thr Asn Thr Gly Ser Tyr Ser Asp
                85                  90                  95

Tyr Ser Met Cys Tyr Ser Met Gly Thr Ala Asp Asn Leu Phe Pro Ser
            100                 105                 110

Gly Asp Phe Glu Arg Ile Trp Thr Gln Tyr Phe Asp Arg Trp Tyr Thr
        115                 120                 125

Ala Ser Arg Ala Val Ala Arg Glu Val Leu Arg Ala Thr Gly Thr Glu
    130                 135                 140

Pro Asp Gly Gly Val Glu Ala Phe Leu Asp Cys Glu Pro Leu Leu Arg
145                 150                 155                 160

Phe Arg Tyr Phe Pro Gln Val Pro Glu His Arg Ser Ala Glu Glu Gln
                165                 170                 175

Pro Leu Arg Met Ala Pro His Tyr Asp Leu Ser Met Val Thr Leu Ile
            180                 185                 190

Gln Gln Thr Pro Cys Ala Asn Gly Phe Val Ser Leu Gln Ala Glu Val
        195                 200                 205

Gly Gly Ala Phe Thr Asp Leu Pro Tyr Arg Pro Asp Ala Val Leu Val
    210                 215                 220

Phe Cys Gly Ala Ile Ala Thr Leu Val Thr Gly Gly Gln Val Lys Ala
225                 230                 235                 240

Pro Arg His His Val Ala Ala Pro Arg Arg Asp Gln Ile Ala Gly Ser
                245                 250                 255

Ser Arg Thr Ser Ser Val Phe Phe Leu Arg Pro Asn Ala Asp Phe Thr
            260                 265                 270

Phe Ser Val Pro Leu Ala Arg Glu Cys Gly Phe Asp Val Ser Leu Asp
        275                 280                 285

Gly Glu Thr Ala Thr Phe Gln Asp Trp Ile Gly Gly Asn Tyr Val Asn
    290                 295                 300

Ile Arg Arg Thr Ser Lys Ala
305                 310

<210> SEQ ID NO 19
<211> LENGTH: 311
<212> TYPE: PRT
<213> ORGANISM: Artificial Sequence
<220> FEATURE:
<223> OTHER INFORMATION: SC-Q126Y mutant

<400> SEQUENCE: 19

Met Asp Thr Thr Val Pro Thr Phe Ser Leu Ala Glu Leu Gln Gln Gly
1               5                   10                  15

Leu His Gln Asp Glu Phe Arg Arg Cys Leu Arg Asp Lys Gly Leu Phe
            20                  25                  30

Tyr Leu Thr Asp Cys Gly Leu Thr Asp Thr Glu Leu Lys Ser Ala Lys
        35                  40                  45
```

```
Asp Leu Val Ile Asp Phe Phe Glu His Gly Ser Glu Ala Glu Lys Arg
         50                  55                  60

Ala Val Thr Ser Pro Val Pro Thr Met Arg Arg Gly Phe Thr Gly Leu
 65                  70                  75                  80

Glu Ser Glu Ser Thr Ala Gln Ile Thr Asn Thr Gly Ser Tyr Ser Asp
                 85                  90                  95

Tyr Ser Met Cys Tyr Ser Met Gly Thr Ala Asp Asn Leu Phe Pro Ser
                100                 105                 110

Gly Asp Phe Glu Arg Ile Trp Thr Gln Tyr Phe Asp Arg Tyr Tyr Thr
            115                 120                 125

Ala Ser Arg Ala Val Ala Arg Glu Val Leu Arg Ala Thr Gly Thr Glu
        130                 135                 140

Pro Asp Gly Gly Val Glu Ala Phe Leu Asp Cys Glu Pro Leu Leu Arg
145                 150                 155                 160

Phe Arg Tyr Phe Pro Gln Val Pro Glu His Arg Ser Ala Glu Glu Gln
                165                 170                 175

Pro Leu Arg Met Ala Pro His Tyr Asp Leu Ser Met Val Thr Leu Ile
            180                 185                 190

Gln Gln Thr Pro Cys Ala Asn Gly Phe Val Ser Leu Gln Ala Glu Val
        195                 200                 205

Gly Gly Ala Phe Thr Asp Leu Pro Tyr Arg Pro Asp Ala Val Leu Val
    210                 215                 220

Phe Cys Gly Ala Ile Ala Thr Leu Val Thr Gly Gln Val Lys Ala
225                 230                 235                 240

Pro Arg His His Val Ala Ala Pro Arg Arg Asp Gln Ile Ala Gly Ser
                245                 250                 255

Ser Arg Thr Ser Ser Val Phe Phe Leu Arg Pro Asn Ala Asp Phe Thr
            260                 265                 270

Phe Ser Val Pro Leu Ala Arg Glu Cys Gly Phe Asp Val Ser Leu Asp
        275                 280                 285

Gly Glu Thr Ala Thr Phe Gln Asp Trp Ile Gly Gly Asn Tyr Val Asn
    290                 295                 300

Ile Arg Arg Thr Ser Lys Ala
305                 310
```

<210> SEQ ID NO 20
<211> LENGTH: 311
<212> TYPE: PRT
<213> ORGANISM: Artificial Sequence
<220> FEATURE:
<223> OTHER INFORMATION: SC-T42DQ126F mutant

<400> SEQUENCE: 20

```
Met Asp Thr Thr Val Pro Thr Phe Ser Leu Ala Glu Leu Gln Gln Gly
 1               5                  10                  15

Leu His Gln Asp Glu Phe Arg Arg Cys Leu Arg Asp Lys Gly Leu Phe
            20                  25                  30

Tyr Leu Thr Asp Cys Gly Leu Thr Asp Asp Glu Leu Lys Ser Ala Lys
         35                  40                  45

Asp Leu Val Ile Asp Phe Glu His Gly Ser Glu Ala Glu Lys Arg
         50                  55                  60

Ala Val Thr Ser Pro Val Pro Thr Met Arg Arg Gly Phe Thr Gly Leu
 65                  70                  75                  80

Glu Ser Glu Ser Thr Ala Gln Ile Thr Asn Thr Gly Ser Tyr Ser Asp
                 85                  90                  95
```

```
Tyr Ser Met Cys Tyr Ser Met Gly Thr Ala Asp Asn Leu Phe Pro Ser
                100                 105                 110

Gly Asp Phe Glu Arg Ile Trp Thr Gln Tyr Phe Asp Arg Phe Tyr Thr
            115                 120                 125

Ala Ser Arg Ala Val Ala Arg Glu Val Leu Arg Ala Thr Gly Thr Glu
130                 135                 140

Pro Asp Gly Gly Val Glu Ala Phe Leu Asp Cys Glu Pro Leu Leu Arg
145                 150                 155                 160

Phe Arg Tyr Phe Pro Gln Val Pro Glu His Arg Ser Ala Glu Glu Gln
                165                 170                 175

Pro Leu Arg Met Ala Pro His Tyr Asp Leu Ser Met Val Thr Leu Ile
            180                 185                 190

Gln Gln Thr Pro Cys Ala Asn Gly Phe Val Ser Leu Gln Ala Glu Val
        195                 200                 205

Gly Gly Ala Phe Thr Asp Leu Pro Tyr Arg Pro Asp Ala Val Leu Val
210                 215                 220

Phe Cys Gly Ala Ile Ala Thr Leu Val Thr Gly Gly Gln Val Lys Ala
225                 230                 235                 240

Pro Arg His His Val Ala Ala Pro Arg Arg Asp Gln Ile Ala Gly Ser
                245                 250                 255

Ser Arg Thr Ser Ser Val Phe Phe Leu Arg Pro Asn Ala Asp Phe Thr
            260                 265                 270

Phe Ser Val Pro Leu Ala Arg Glu Cys Gly Phe Asp Val Ser Leu Asp
        275                 280                 285

Gly Glu Thr Ala Thr Phe Gln Asp Trp Ile Gly Gly Asn Tyr Val Asn
290                 295                 300

Ile Arg Arg Thr Ser Lys Ala
305                 310

<210> SEQ ID NO 21
<211> LENGTH: 32
<212> TYPE: DNA
<213> ORGANISM: Artificial Sequence
<220> FEATURE:
<223> OTHER INFORMATION: penicillin expandase forward primer

<400> SEQUENCE: 21
gaccatatgg ataccacggt accgacattt tc                             32

<210> SEQ ID NO 22
<211> LENGTH: 37
<212> TYPE: DNA
<213> ORGANISM: Artificial Sequence
<220> FEATURE:
<223> OTHER INFORMATION: penicillin expandase reverse primer

<400> SEQUENCE: 22
gcaagatctt taagctttac tcgtacgacg aatgttc                        37

<210> SEQ ID NO 23
<211> LENGTH: 37
<212> TYPE: DNA
<213> ORGANISM: Artificial Sequence
<220> FEATURE:
<223> OTHER INFORMATION: penicillin expandase forward primer

<400> SEQUENCE: 23
gaccgattgt ggcctgacag attgcgaact gaaatct                        37
```

<210> SEQ ID NO 24
<211> LENGTH: 37
<212> TYPE: DNA
<213> ORGANISM: Artificial Sequence
<220> FEATURE:
<223> OTHER INFORMATION: penicillin expandase reverse primer

<400> SEQUENCE: 24
agatttcagt tcgcaatctg tcaggccaca atcggtc        37

<210> SEQ ID NO 25
<211> LENGTH: 37
<212> TYPE: DNA
<213> ORGANISM: Artificial Sequence
<220> FEATURE:
<223> OTHER INFORMATION: penicillin expandase forward primer

<400> SEQUENCE: 25
gaccgattgt ggcctgacag atgatgaact gaaatct        37

<210> SEQ ID NO 26
<211> LENGTH: 37
<212> TYPE: DNA
<213> ORGANISM: Artificial Sequence
<220> FEATURE:
<223> OTHER INFORMATION: penicillin expandase reverse primer

<400> SEQUENCE: 26
agatttcagt tcatcatctg tcaggccaca atcggtc        37

<210> SEQ ID NO 27
<211> LENGTH: 37
<212> TYPE: DNA
<213> ORGANISM: Artificial Sequence
<220> FEATURE:
<223> OTHER INFORMATION: penicillin expandase forward primer

<400> SEQUENCE: 27
gaccgattgt ggcctgacag atgaagaact gaaatct        37

<210> SEQ ID NO 28
<211> LENGTH: 37
<212> TYPE: DNA
<213> ORGANISM: Artificial Sequence
<220> FEATURE:
<223> OTHER INFORMATION: penicillin expandase reverse primer

<400> SEQUENCE: 28
agatttcagt tcttcatctg tcaggccaca atcggtc        37

<210> SEQ ID NO 29
<211> LENGTH: 37
<212> TYPE: DNA
<213> ORGANISM: Artificial Sequence
<220> FEATURE:
<223> OTHER INFORMATION: penicillin expandase forward primer

<400> SEQUENCE: 29
gaccgattgt ggcctgacag atatggaact gaaatct        37

<210> SEQ ID NO 30
<211> LENGTH: 37
<212> TYPE: DNA
<213> ORGANISM: Artificial Sequence
<220> FEATURE:
<223> OTHER INFORMATION: penicillin expandase reverse primer

```
<400> SEQUENCE: 30
agatttcagt tccatatctg tcaggccaca atcggtc                                    37

<210> SEQ ID NO 31
<211> LENGTH: 37
<212> TYPE: DNA
<213> ORGANISM: Artificial Sequence
<220> FEATURE:
<223> OTHER INFORMATION: penicillin expandase forward primer

<400> SEQUENCE: 31
gaccgattgt ggcctgacag atccggaact gaaatct                                    37

<210> SEQ ID NO 32
<211> LENGTH: 37
<212> TYPE: DNA
<213> ORGANISM: Artificial Sequence
<220> FEATURE:
<223> OTHER INFORMATION: penicillin expandase reverse primer

<400> SEQUENCE: 32
agatttcagt tccggatctg tcaggccaca atcggtc                                    37

<210> SEQ ID NO 33
<211> LENGTH: 37
<212> TYPE: DNA
<213> ORGANISM: Artificial Sequence
<220> FEATURE:
<223> OTHER INFORMATION: penicillin expandase forward primer

<400> SEQUENCE: 33
gaccgattgt ggcctgacag atcaggaact gaaatct                                    37

<210> SEQ ID NO 34
<211> LENGTH: 37
<212> TYPE: DNA
<213> ORGANISM: Artificial Sequence
<220> FEATURE:
<223> OTHER INFORMATION: penicillin expandase reverse primer

<400> SEQUENCE: 34
agatttcagt tcctgatctg tcaggccaca atcggtc                                    37

<210> SEQ ID NO 35
<211> LENGTH: 37
<212> TYPE: DNA
<213> ORGANISM: Artificial Sequence
<220> FEATURE:
<223> OTHER INFORMATION: penicillin expandase forward primer

<400> SEQUENCE: 35
gaccgattgt ggcctgacag atcgcgaact gaaatct                                    37

<210> SEQ ID NO 36
<211> LENGTH: 37
<212> TYPE: DNA
<213> ORGANISM: Artificial Sequence
<220> FEATURE:
<223> OTHER INFORMATION: penicillin expandase reverse primer

<400> SEQUENCE: 36
agatttcagt tcgcgatctg tcaggccaca atcggtc                                    37

<210> SEQ ID NO 37
```

```
<210> SEQ ID NO 37
<211> LENGTH: 37
<212> TYPE: DNA
<213> ORGANISM: Artificial Sequence
<220> FEATURE:
<223> OTHER INFORMATION: penicillin expandase forward primer

<400> SEQUENCE: 37
ctggacgcag tattttgatc gcgcgtatac cgccagt                        37

<210> SEQ ID NO 38
<211> LENGTH: 37
<212> TYPE: DNA
<213> ORGANISM: Artificial Sequence
<220> FEATURE:
<223> OTHER INFORMATION: penicillin expandase reverse primer

<400> SEQUENCE: 38
actggcggta tacgcgcgat caaaatactg cgtccag                        37

<210> SEQ ID NO 39
<211> LENGTH: 37
<212> TYPE: DNA
<213> ORGANISM: Artificial Sequence
<220> FEATURE:
<223> OTHER INFORMATION: penicillin expandase forward primer

<400> SEQUENCE: 39
ctggacgcag tattttgatc gcttttatac cgccagt                        37

<210> SEQ ID NO 40
<211> LENGTH: 37
<212> TYPE: DNA
<213> ORGANISM: Artificial Sequence
<220> FEATURE:
<223> OTHER INFORMATION: penicillin expandase reverse primer

<400> SEQUENCE: 40
actggcggta taaaagcgat caaaatactg cgtccag                        37

<210> SEQ ID NO 41
<211> LENGTH: 37
<212> TYPE: DNA
<213> ORGANISM: Artificial Sequence
<220> FEATURE:
<223> OTHER INFORMATION: penicillin expandase forward primer

<400> SEQUENCE: 41
ctggacgcag tattttgatc gcatttatac cgccagt                        37

<210> SEQ ID NO 42
<211> LENGTH: 37
<212> TYPE: DNA
<213> ORGANISM: Artificial Sequence
<220> FEATURE:
<223> OTHER INFORMATION: penicillin expandase reverse primer

<400> SEQUENCE: 42
actggcggta taaatgcgat caaaatactg cgtccag                        37

<210> SEQ ID NO 43
<211> LENGTH: 37
<212> TYPE: DNA
<213> ORGANISM: Artificial Sequence
<220> FEATURE:
<223> OTHER INFORMATION: penicillin expandase forward primer

<400> SEQUENCE: 43
```
ctggacgcag tattttgatc gcctgtatac cgccagt        37

<210> SEQ ID NO 44
<211> LENGTH: 37
<212> TYPE: DNA
<213> ORGANISM: Artificial Sequence
<220> FEATURE:
<223> OTHER INFORMATION: penicillin expandase reverse primer

<400> SEQUENCE: 44
actggcggta tacaggcgat caaaatactg cgtccag        37

<210> SEQ ID NO 45
<211> LENGTH: 37
<212> TYPE: DNA
<213> ORGANISM: Artificial Sequence
<220> FEATURE:
<223> OTHER INFORMATION: penicillin expandase forward primer

<400> SEQUENCE: 45
ctggacgcag tattttgatc gcatgtatac cgccagt        37

<210> SEQ ID NO 46
<211> LENGTH: 37
<212> TYPE: DNA
<213> ORGANISM: Artificial Sequence
<220> FEATURE:
<223> OTHER INFORMATION: penicillin expandase reverse primer

<400> SEQUENCE: 46
actggcggta tacatgcgat caaaatactg cgtccag        37

<210> SEQ ID NO 47
<211> LENGTH: 37
<212> TYPE: DNA
<213> ORGANISM: Artificial Sequence
<220> FEATURE:
<223> OTHER INFORMATION: penicillin expandase forward primer

<400> SEQUENCE: 47
ctggacgcag tattttgatc gcaactatac cgccagt        37

<210> SEQ ID NO 48
<211> LENGTH: 37
<212> TYPE: DNA
<213> ORGANISM: Artificial Sequence
<220> FEATURE:
<223> OTHER INFORMATION: penicillin expandase reverse primer

<400> SEQUENCE: 48
actggcggta tagttgcgat caaaatactg cgtccag        37

<210> SEQ ID NO 49
<211> LENGTH: 37
<212> TYPE: DNA
<213> ORGANISM: Artificial Sequence
<220> FEATURE:
<223> OTHER INFORMATION: penicillin expandase forward primer

<400> SEQUENCE: 49
ctggacgcag tattttgatc gctggtatac cgccagt        37

<210> SEQ ID NO 50
<211> LENGTH: 37
<212> TYPE: DNA

```
<213> ORGANISM: Artificial Sequence
<220> FEATURE:
<223> OTHER INFORMATION: penicillin expandase reverse primer

<400> SEQUENCE: 50
actggcggta taccagcgat caaaatactg cgtccag                              37

<210> SEQ ID NO 51
<211> LENGTH: 37
<212> TYPE: DNA
<213> ORGANISM: Artificial Sequence
<220> FEATURE:
<223> OTHER INFORMATION: penicillin expandase forward primer

<400> SEQUENCE: 51
ctggacgcag tattttgatc gctattatac cgccagt                              37

<210> SEQ ID NO 52
<211> LENGTH: 37
<212> TYPE: DNA
<213> ORGANISM: Artificial Sequence
<220> FEATURE:
<223> OTHER INFORMATION: penicillin expandase reverse primer

<400> SEQUENCE: 52
actggcggta taatagcgat caaaatactg cgtccag                              37
```